(12) United States Patent
Wong

(10) Patent No.: US 10,816,478 B2
(45) Date of Patent: Oct. 27, 2020

(54) URINARY POLYAMINES AS PROSTATE CANCER DETECTION BIOMARKERS

(71) Applicant: New Life Medicine Technology Company Limited, Hong Kong (HK)

(72) Inventor: Ka Leung Wong, Hong Kong (HK)

(73) Assignee: New Life Medicine Technology Company Limited, Hong Kong (CN)

( * ) Notice: Subject to any disclaimer, the term of this patent is extended or adjusted under 35 U.S.C. 154(b) by 362 days.

(21) Appl. No.: 15/953,572

(22) Filed: Apr. 16, 2018

(65) Prior Publication Data

US 2018/0252652 A1 Sep. 6, 2018

Related U.S. Application Data

(63) Continuation-in-part of application No. 15/784,269, filed on Oct. 16, 2017, now Pat. No. 10,527,627.

(60) Provisional application No. 62/409,361, filed on Oct. 17, 2016, provisional application No. 62/471,989, filed on Mar. 16, 2017, provisional application No. 62/626,149, filed on Feb. 4, 2018.

(51) Int. Cl.
| | | |
|---|---|---|
| *G01N 21/00* | (2006.01) |
| *G01N 21/78* | (2006.01) |
| *G01N 33/493* | (2006.01) |
| *G01N 21/76* | (2006.01) |
| *G01N 33/52* | (2006.01) |
| *G01N 33/574* | (2006.01) |
| *C07D 403/14* | (2006.01) |

(52) U.S. Cl.
CPC .......... *G01N 21/78* (2013.01); *C07D 403/14* (2013.01); *G01N 21/76* (2013.01); *G01N 33/493* (2013.01); *G01N 33/52* (2013.01); *G01N 33/57434* (2013.01); *G01N 2800/342* (2013.01); *G01N 2800/50* (2013.01)

(58) Field of Classification Search
CPC ...................................................... G01N 21/78
USPC ............................................................ 436/64
See application file for complete search history.

(56) References Cited

PUBLICATIONS

Zhuang et al. Photo-reactive charge trapping memory based on lanthanide complex Sci. Rep. 5, 14998; doi: 10.1038/srep14998 (2015). (Year: 2015).*

Kadjane et al. "Improving Visible Light Sensitization of Luminescent Europium Complexes" J Fluoresc (2008) 18:119-129 (Year: 2008).*

First Examination Report with Search Report of TW App. No. 107112944 issued by the Taiwan Intellectual Property Office (TIPO) of the ROC dated Jun. 4, 2019.

Tsoi et al.; Urinary Polyamines: A Pilot Study on Their Roles as Prostate Cancer Detection Biomarkers; PLOS ONE; Sep. 6, 2016; DOI:10.1371/journal.pone.0162217.

(Continued)

*Primary Examiner* — Christine T Mui
*Assistant Examiner* — Emily R. Berkeley
(74) *Attorney, Agent, or Firm* — Spruson & Ferguson (Hong Kong) Limited

(57) ABSTRACT

Luminescent lanthanide complexes comprising a triazine-based ligand capable of selective detection of urinary polyamines and their methods of use in detecting and quantifying urinary polyamines as well as prostate cancer biomarkers, such as spermine. The detection of the urinary polyamines can be accomplished using colorimetric methods such as, with an ultraviolet-visible spectrometer.

20 Claims, 26 Drawing Sheets

(56) References Cited

PUBLICATIONS

Abergel et al.; Using the Antenna Effect as a Spectroscopic Tool: Photophysics and Solution Thermodynamics of the Model Luminescent Hydroxypyridonate Complex [Eu111(3,4,3-LI(1,2-Hopo))]-; Inorganic Chemistry; Dec. 7, 2009; vol. 48, Issue 23; ACS Publications.

* cited by examiner

| Sample No. | Conc/ppm | Sample No. | Conc/ppm |
|---|---|---|---|
| 1 | 4.14 | 6 | 0.38 |
| 2 | 1.97 | 7 | 0.36 |
| 3 | 0.63 | 8 | 0.31 |
| 4 | 0.66 | 9 | 2.04 |
| 5 | 0.37 | 10 | 1.14 |

Figure 9B

URINARY POLYAMINES AS PROSTATE CANCER DETECTION BIOMARKERS

CROSS-REFERENCE TO RELATED APPLICATIONS

The present application is a continuation-in-part application of U.S. Non-provisional patent application Ser. No. 15/784,269, filed on Oct. 16, 2017, which claims priority from U.S. Provisional Patent Application Ser. No. 62/409,361, filed on Oct. 17, 2016, and U.S. Provisional Patent Application Ser. No. 62/471,989, filed on Mar. 16, 2017. This application also claims priority from U.S. Provisional Patent Application Ser. No. 62/626,149, filed on Feb. 4, 2018. The disclosures of all the above referenced patent applications are hereby incorporated by reference in their entirety.

FIELD OF THE INVENTION

The present disclosure relates to methods for the detection and quantization of urinary polyamines and compositions for use therein. The methods and compositions described herein are useful in diagnosis of prostate cancer in patient.

BACKGROUND OF THE INVENTION

Prostate cancer (PCa) is the second most common cancer in men, and is one of the leading causes of mortality and results in momentous public health impact in many developed countries, including many Western European nations and the United States.

PCa is a disease of increasing significance worldwide. No exception is Hong Kong in this public health issue. With reference to the statistics of Hong Kong Cancer Registry, Hospital Authority, HKSAR, PCa ranked $3^{rd}$ for the most common cancers in men and $5^{th}$ for the most fatal cancers. Given the latency of early, treatable PCa and the lethality of its late and discernible stage, there is an urgent need for more sensitive and accurate diagnostic methods to detect early stage PCa, so that treatment outcome can be significantly improved with more lives being saved.

Current diagnosis of PCa relies on digital rectal examination (DRE) and serum prostate specific antigen (PSA) test, followed by transrectal ultrasound prostatic biopsy (TRUSPB) confirmation. Although DRE is a simple procedure, it causes discomfort to patients. DRE is also a strong-investigator-dependent technique, which results in poor accuracy for PCa diagnosis. In particular, DRE is not a good tool for the early detection of PCa, because most DRE positive PCa results are of advanced staging. Although the PSA test shows good sensitivity in detecting early stage PCa, elevated PSA levels have also been observed in patients with benign prostatic hyperplasia (BPH) and prostatitis, etc., which decreases the specificity of PSA for PCa.

Within the grey zone of the PSA test, the positive-predictive value has a small mean value of 21%. A wide variety of PSA methodologies, such as the PSA density of transition zone, free/total PSA ratio, p2PSA and Prostate Health Index have been developed to improve the performance of PSA measurement.

Transrectal ultrasonography guided prostate biopsy (TRUSPB) is currently the most common diagnostic approach for histological confirmation of PCa diagnosis. However, this procedure is very labor intensive and leads to significant discomfort and complications to patients.

As a result of the poor specificity of serum PSA test, many patients without PCa are subjected to TRUSPB and thus its potential complications. It is therefore essential to develop a more efficient detection kit for accurate, early stage PCa screening.

It is an objective of the present disclosure to provide a method for diagnosing PCa in a patient comprising detecting one or more urinary polyamines (such as, putrescine (Put), spermindine (Spd) and/or spermine (Spm)). The urinary polyamines are useful as biomarkers for PCa detection. The diagnostic power of the urinary polyamines was identified by comparing urinary polyamine concentrations in patients diagnosed with PCa, patients diagnosed with benign prostatic hyperplasia (BPH) and healthy controls (HC). Also provided herein are compositions and methods useful for detecting and quantifying the amount of the urinary polyamines in a patient.

SUMMARY OF THE INVENTION

Accordingly, the objective of this disclosure is to develop a novel, highly-sensitive and specific, and colour-changing polyamines tracer with the use of lanthanide complexes, and to examine the averaged urinary concentrations of polyamines from patients of different age groups and stages of prostate cancer to validate polyamines as a trustworthy biomarkers for early prostate cancer screening.

In a first aspect of the present disclosure, there is provided is a compound of formula of Formula 1:

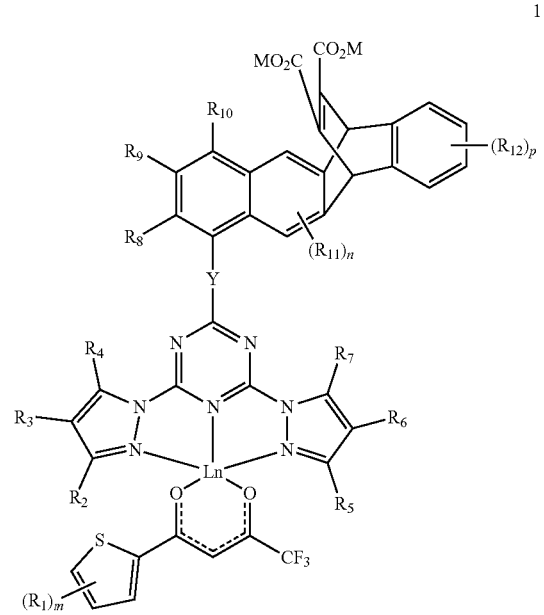

wherein m is 1, 2, or 3;
n for each occurrence is independently 1 or 2;
p for each occurrence is independently is 1, 2, 3, or 4;

Ln is a lanthanide;

each M is independently selected from the group consisting of Na, Li, and K; or two M taken together represent Mg or Ca;

Y is —C≡C— or is absent;

$R_1$ for each instance is independently hydrogen, alkyl, or cycloalkyl;

each of $R_2$, $R_3$, $R_4$, $R_5$, $R_6$, and $R_7$ are independently selected from hydrogen, alkyl, cycloalkyl and aryl;

each of $R_8$ and $R_9$ are independently selected from hydrogen, halide, cyano, nitro, hydroxyl, ether, thioether, amine, amide, acylamino, ester, alkyl, cycloalkyl, heterocycloalkyl, aryl, heteroaryl, alkene, and alkyne; or $R_8$ and $R_9$ taken together form a moiety selected from the group consisting of:

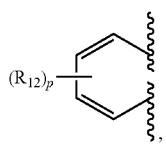 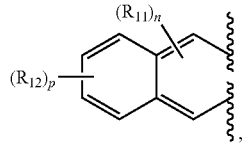 and

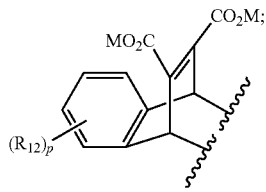

$R_{10}$ is hydrogen, halide, cyano, nitro, hydroxyl, ether, thioether, amine, amide, acylamino, ester, alkyl, cycloalkyl, heterocycloalkyl, aryl, heteroaryl, alkene, or alkyne; or $R_{10}$ is a moiety having the structure:

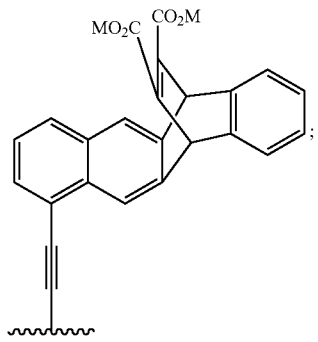

and for each instance of $R_{11}$ and $R_{12}$ is independently selected from hydrogen, halide, cyano, nitro, hydroxyl, ether, thioether, amine, amide, acylamino, ester, alkyl, cycloalkyl, heterocycloalkyl, aryl, heteroaryl, alkene, and alkyne; with the proviso that the compound of Formula 1 does not include a compound of Formula 2:

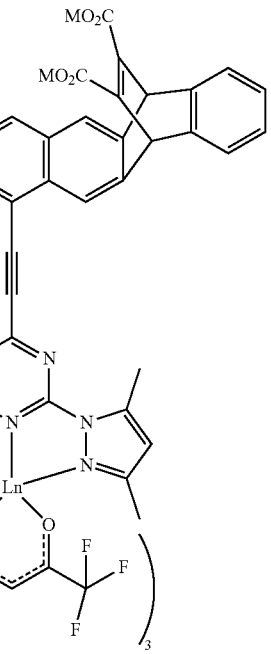

wherein, Ln is a lanthanide; and each M is independently selected from the group consisting of Na, Li, and K; or two M taken together represent Mg or Ca.

In a first embodiment of the first aspect, provided is the compound of the first aspect, wherein each of $R_2$, $R_3$, $R_4$, $R_5$, $R_6$, and $R_7$ are independently selected from hydrogen and alkyl.

In a second embodiment of the first aspect, provided is the compound of the first aspect, wherein each instance of $R_{11}$ and $R_{12}$ is independently hydrogen, halide, nitro, cyano, ether, or alkyl.

In a third embodiment of the first aspect, provided is the compound of the first aspect, wherein each of $R_8$ and $R_9$ is independently selected from hydrogen, halide, nitro, cyano, ether, and alkyl; or $R_8$ and $R_9$ taken together form a moiety selected from the group consisting of:

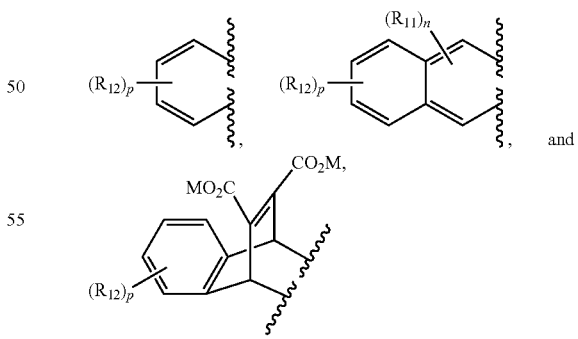

wherein each instance of $R_{11}$ and $R_{12}$ is independently hydrogen, halide, nitro, cyano, ether, or alkyl.

In a fourth embodiment of the first aspect, provided is the compound of the first aspect, wherein $R_{10}$ is hydrogen, halide, nitro, cyano, ether, dialkyl amino, or alkyl; or $R_{10}$ is a moiety having the structure:

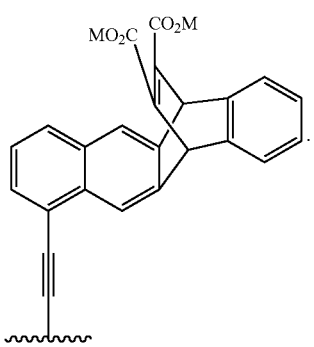

In a fifth embodiment of the first aspect, provided is the compound of the first embodiment of the first aspect, wherein each instance of $R_1$, $R_3$, and $R_6$ are hydrogen.

In a fifth embodiment of the first aspect, provided is the compound of the second embodiment of the first aspect, wherein each of $R_8$ and $R_9$ is independently selected from hydrogen, halide, nitro, cyano, ether, and alkyl; or $R_8$ and $R_9$ taken together form a moiety selected from the group consisting of:

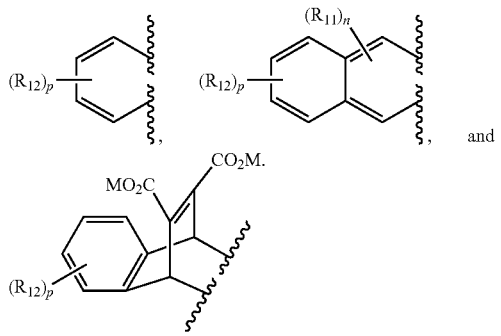

In a sixth embodiment of the first aspect, provided is the compound of the second embodiment of the first aspect, wherein $R_{10}$ is hydrogen, halide, nitro, cyano, ether, dialkyl amino, or alkyl; or $R_{10}$ is a moiety having the structure:

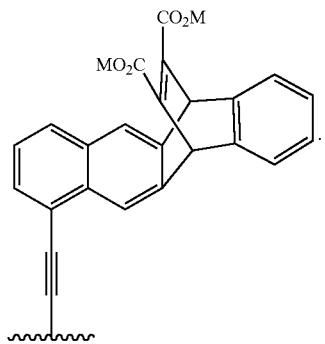

In a seventh embodiment of the first aspect, provided is the compound the first aspect, wherein m is 1, 2, or 3; n for each occurrence is independently 1 or 2; p for each occurrence is independently is 1, 2, 3, or 4;

Ln is a lanthanide;

each M is independently selected from the group consisting of Na, Li, and K; or two M taken together represent Mg or Ca;

Y is —C≡C—;

$R_1$ for each instance is independently hydrogen or alkyl;

each of $R_2$, $R_3$, $R_4$, $R_5$, $R_6$, and $R_7$ are independently selected from hydrogen and alkyl;

each of $R_8$ and $R_9$ are independently selected from hydrogen and alkyl; or $R_8$ and $R_9$ taken together form a moiety selected from the group consisting of:

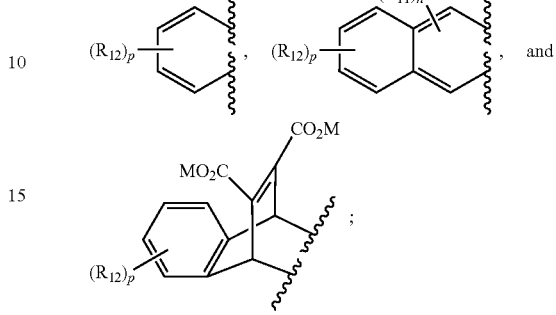

$R_{10}$ is hydrogen, alkyl, and amine; or $R_{10}$ is a moiety having the structure:

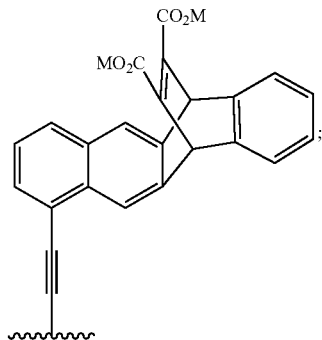

and for each instance of $R_1$ and $R_{12}$ is independently selected from hydrogen and alkyl.

In a seventh embodiment of the first aspect, provided is the compound of the first aspect, wherein the compound is selected from the group consisting of:

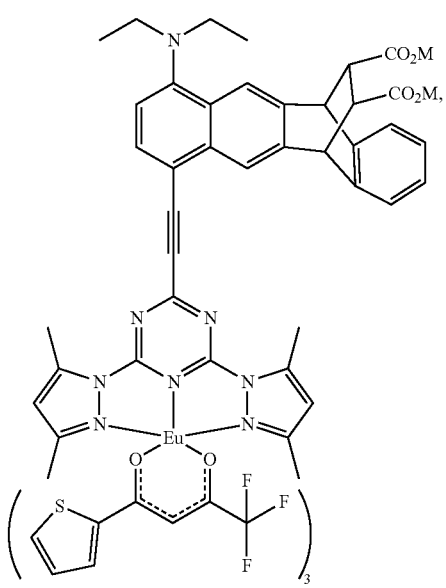

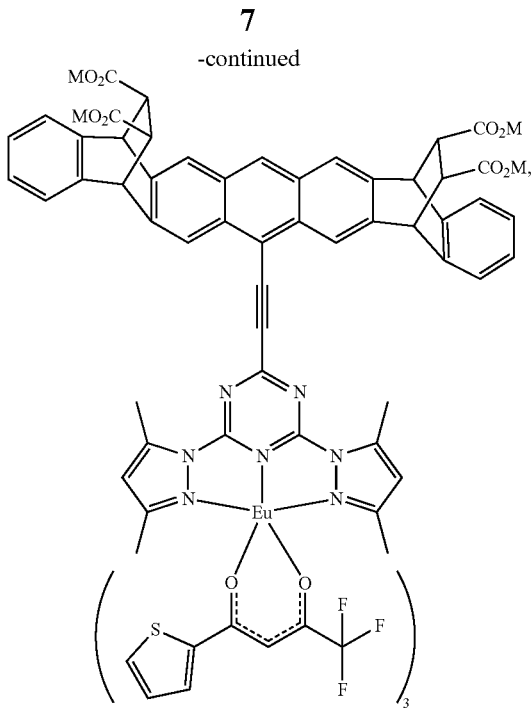

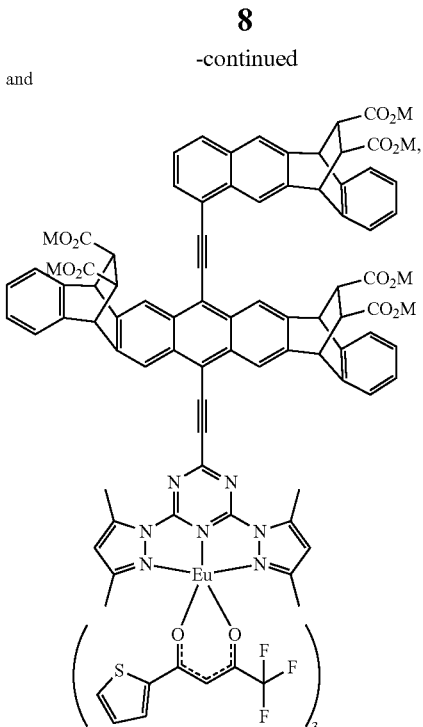

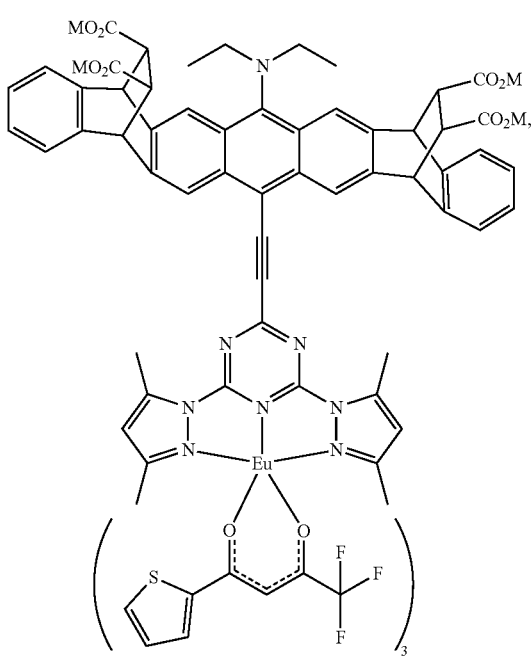

wherein M is lithium or sodium.

In a second aspect of the present disclosure, there is provided is a method of detecting one or more urinary polyamines, comprising the steps of:
a. providing a urine sample;
b. contacting the urine sample with a compound of Formula 1 thereby forming a test sample; and
c. detecting the presence of the one or more urinary polyamines in the test sample.

In a first embodiment of the second aspect, provided herein is the method of the second aspect, wherein the urine sample is obtained from an individual.

In a second embodiment of the second aspect, provided herein is the method of the first embodiment of the second aspect, wherein the one or more urinary polyamines is spermine.

In a third embodiment of the second aspect, provided herein is the method of the first embodiment of the second aspect, wherein the step of detecting the presence of the one or more urinary polyamines comprises determining the concentration of the one or more urinary polyamines.

In a fourth embodiment of the second aspect, provided herein is the method of the third embodiment of the second aspect, wherein the one or more urinary polyamines is spermine.

In a fifth embodiment of the second aspect, provided herein is the method of the fourth embodiment of the second aspect further comprising the step of comparing the concentration of spermine in the test sample with a reference concentration and determining whether the individual has an increased susceptibility to prostate cancer, wherein a decrease in the concentration of spermine in the test sample relative to the reference sample indicates an increased susceptibility to prostate cancer in the individual.

In a sixth embodiment of the second aspect, provided herein is the method of the fifth embodiment of the second aspect further comprising the step of conducting a prostate exam on the individual to determine if the individual has prostate cancer and treat the individual with radiotherapy or chemotherapy if the individual has prostate cancer.

In a third aspect of the present disclosure, there is provided is a method for treating prostate cancer in an individual comprising the steps of:
d. providing a urine sample from the individual;
e. contacting the urine sample with a compound of Formula 1 thereby forming a test sample;
f. determining the concentration of spermine in the test sample;
g. comparing the concentration of spermine in the test sample with a reference concentration and determining whether the individual has an increased susceptibility to prostate cancer, wherein a decrease in the concentration of spermine in the test sample relative to the reference sample indicates an increased susceptibility to prostate cancer in the individual;
h. conducting a prostate exam on the individual to determine if the individual has prostate cancer; and
i. treating the individual with radiotherapy or chemotherapy if the individual has prostate cancer.

In a first embodiment of the third aspect, provided herein is the method of the third aspect, wherein the step of determining the concentration of spermine comprises comparing the color of the test sample with a calibrated reference color chart.

In a second embodiment of the third aspect, provided herein is the method of the third aspect, wherein the individual is a human.

Those skilled in the art will appreciate that the invention described herein is susceptible to variations and modifications other than those specifically described.

The invention includes all such variation and modifications. The invention also includes all of the steps and features referred to or indicated in the specification, individually or collectively, and any and all combinations or any two or more of the steps or features.

Other aspects and advantages of the invention will be apparent to those skilled in the art from a review of the ensuing description.

BRIEF DESCRIPTION OF THE DRAWINGS

The above and other objects and features of the present disclosure will become apparent from the following description of the various embodiments described herein, when taken in conjunction with the accompanying drawings, in which:

FIG. 9B shows the concentration of Spm level in 10 selected prostate cancer patients' urine samples for UV test.

DETAILED DESCRIPTION OF THE INVENTION

Figure 1:
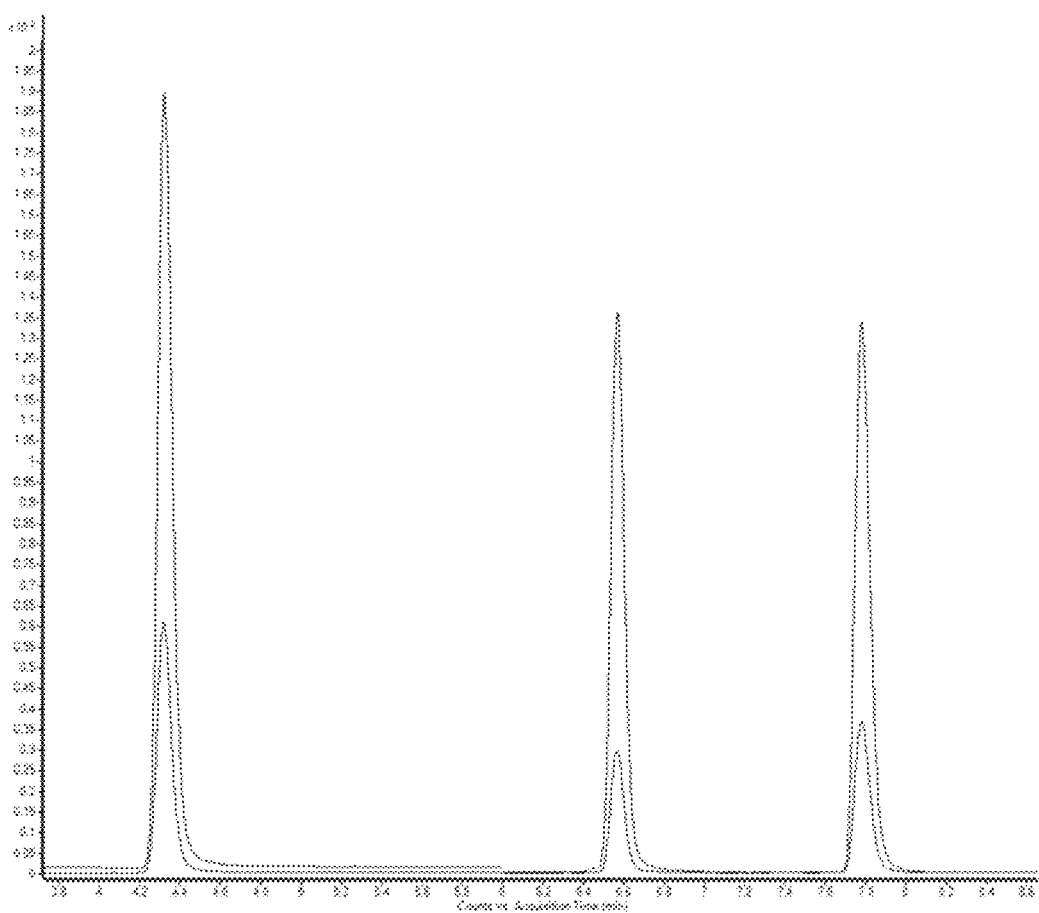
FIG. 1 shows the overlaid UPLC-MS/MS SRM chromatograms of 1,000 ppb mixed polyamines standard (0-10 mins being shown). Put (Large peak, $t_R$=4.3 min), Put-$d_8$ (Small peak, $t_R$=4.3 min), Spd (Large peak, $t_R$=6.6 min), Spd-$d_8$ (Small peak, $t_R$=6.6 min), Spm (Large peak, $t_R$=7.8 min) and Spm-$d_8$ (Small peak, $t_R$=7.8 min).

The present disclosure is not to be limited in scope by any of the specific embodiments described herein. The following embodiments are presented for exemplification only.

Three urinary polyamines (Put, Spd and Spm) were evaluated as biomarkers for PCa detection by comparing the concentrations of each in patients diagnosed with PCa, BPH patients and healthy patients. Through a well validated chromatographic method, urinary Spm had been shown to possess usefulness in differentiating PCa from non-cancerous disease states including BPH, and it could help to act as a secondary screening tool to serum PSA test to address its high false-positive rate when using 4.0 ng/mL as a cut-off point. A kit comprising a lanthanide complex was developed towards this novel biomarker and is described herein.

Part 1: Evaluation of Polyamines' Roles as PCa Biomarker
Clinical Samples

Three subsets of patients for the clinical samples collection were assigned as follows: patients diagnosed with PCa, patients diagnosed with BPH, and HC. Written consent was acquired from all of the subjects. Enrolment of patients into the clinical study was reviewed and approved by the Clinical Research Ethical Committee of the Chinese University of Hong Kong, and the study was performed strictly according to the guidelines developed by that committee. Urine samples were obtained at noon time after lunch prior to prostatic biopsy from 165 male patients (age >50) having serum PSA level greater than 4.0 ng/mL between October 2014 and March 2016. These patients' urine samples were accepted only when they didn't have clinically active urinary tract infection which might pose a biasing effect. When patients did not agree to consent for the study, or they clinically showed evidence of other types of cancers, they were excluded from the sampling scheme.

Amongst these 165 patients, 66 were diagnosed as having PCa and the remaining 99 had no evidence of malignancy (NEM) by using TRUSPB as the reference standard. To further categorize these 99 NEM patients, using the criteria of prostate volume >30 mL as criteria, 88 were found to have BPH while others were considered as HC. All pathological examinations were conducted at Prince of Wales Hospital, The Chinese University of Hong Kong, Hong Kong under the supervision of experienced uro-pathologists.

Table 1 shows all the clinicopathologic characteristics of samples. All samples were stored at −20° C. until measurement. All measurements were conducted within three months after collection.

dine (butane-$d_8$) trihydrochloride (98 atom % D, 95% CP), spermine (butane-$d_8$) tetrahydrochloride (97 atom % D, 95% CP) and heptafluorobutyric acid (HFBA, ≥99.0%) were purchased from Sigma-Aldrich (Hong Kong, China) and used without further purification. Strong Anion Exchange solid phase extraction (SPE) cartridges were obtained from Phenomenex (Strata, 100 mg/3 mL, USA). Centrifugation was performed using a Refrigerated centrifuge obtained from Eppendorf (5417R, Hong Kong, China).

Determination of Creatinine

The creatinine concentration inside urine samples were determined by a creatinine assay sold tinder the trademark LabAssay™ Creatinine assay (Wako, Japan). Briefly, urine samples and standards were thawed, deproteinized and centrifuged. The supernatant was separated and reacted with picric acid in alkaline solution to produce tangerine condensate through Jaffe reaction as reported in Bonsnes R W, Taussky H H. *On the colorimetric determination of creatinine by the Jaffé reaction. J Biol Chem.* 1945; 158(3):581-9. Quantitation of total creatinine inside samples was made by measurement of absorbance by a monochromator microplate reader sold under the trademark Clariostar® Monochromator Microplate Reader (BMG Labtech, Hong Kong). Concentrated urine samples which exceeded the calibration points were diluted with water with appropriate dilution factor before sample preparation. Each sample was determined at least twice with Relative standard deviation (RSD) less than 15%.

TABLE 1

Clinicopathologic characteristics of patients.

| Characteristics | PCa (n = 66) | BPH (n = 88) | HC (n = 11) | p value (PCa vs BPH) | p value (PCa vs HC) | p value (BPH vs HC) |
|---|---|---|---|---|---|---|
| Age | | | | | | |
| Mean (SEM) | 69.6 (0.8) | 66.9 (0.6) | 64.9 (1.1) | 0.018 | 0.027 | 0.245 |
| Median | 69 | 66 | 65 | | | |
| Range | 54-86 | 51-79 | 59-74 | | | |
| Preoperative PSA. ng/mL | | | | | | |
| Mean (SEM) | 46.39 (8.61) | 12.39 (1.57) | 26.54 (7.51) | <0.0001 | 0.350 | 0.007 |
| Median | 15.60 | 8.60 | 8.50 | | | |
| Range | 4.20-299.00 | 4.40-98.50 | 4.3-66.00 | | | |
| Gleason score (GS) | | — | — | | | |
| 5 | 1 | | | | | |
| 6 | 26 | | | | | |
| 7 | 15 | | | | | |
| 8 | 10 | | | | | |
| 9 | 12 | | | | | |
| 10 | 2 | | | | | |
| Prostate volume (mL) | | | | | | |
| Mean (SEM) | 43.81 (2.44) | 67.28 (2.98) | 17.46 (2.67) | <0.0001 | <0.0001 | <0.0001 |
| Median | 40.00 | 56.50 | 20.40 | | | |
| Range | 16.60-87.80 | 32.20-162.00 | 4.60-30.00 | | | |

Materials and Chemicals

Methanol was obtained from TEDIA (HPLC/Spectro grade, ≥99.9%). Acetonitrile was obtained from ACS (HPLC grade, ≥99.9%). Water was purified in a water purification system sold under the trademark MilliQ® Direct Water Purification System (Millipore, USA). All standard compounds, including 1,4-Diaminobutane (Put, 99%), spermidine (Spd, ≥99.0%), spermine (Spm, ≥99.0%), 1,4-Diamino(butane-$d_8$) dihydrochloride (98 atom % D), spermi- Exemplary Sample Preparation for Determination of Polyamines Stock solutions (5,000 μg/mL) of each polyamine (Put, Spm, Spd) were prepared in water separately. The three stock solutions were mixed and diluted to give an intermediate standard (50 μg/mL), which was then used to prepare a series of working standards with polyamine concentrations of 10, 25, 50, 100, 250, 500, 1,000 ng/mL in water. For internal standards, the stock solutions (5,000 μg/mL) of each polyamine (Put-d$_8$, Spm-d$_8$, Spd-d$_8$) were prepared in water individually. The three stock solution were mixed and diluted to give an internal standard (IS) working solution (1 µg/mL) in water.

Exemplary Sample Pretreatment for Determination of Polyamines

The sample preparation procedures followed the method developed by Häkkinen et al. *Analysis of free, mono-and diacetylated polyamines from human urine by LC-MS/MS. J Chromatogr B Analyt Technol Biomed Life Sci.* 2013; 941: 81-9 with little modifications. Firstly, urine samples/standards were thawed naturally and centrifuged for 5 minutes at 13,000 rpm and room temperature. 120 µL of urine sample/standard supernatant and 60 µL of IS working solution were mixed with 420 µL of water. 550 µL of this well-mixed solution was passed through the SPE cartridges, which had been conditioned and equilibrated with 1 mL of methanol and water respectively. 450 µL of water was passed through the cartridge afterwards to elute out all polyamines. 400 µL of these SPE treated samples were then mixed with 100 µL of 10% HFBA, and the final mixture was ready for instrumental analysis. Concentrated urine samples which exceeded the calibration points were diluted with water with appropriate dilution factors before sample preparation.

Quality Control Samples for Determination of Polyamines

For each batch of sample analysis, three Quality control (QC) working solutions were analyzed to verify the accuracy of calibration curves and ensure comparability among batches. The solutions were prepared using analyzed control urine samples from our research group. The polyamines concentrations of controls' urine samples were determined and then mixed equally to give a pooled urine sample. Afterwards, three QC working solutions with different polyamine concentration range (low, medium and high) were prepared by mixing this pooled urine sample with standard solutions. For low polyamine concentration QC working solution, the SPE-treated pooled urine sample was mixed with SPE-treated 10 ng/mL standard in the 1:7 ratio. For medium polyamine concentration QC working solution, the SPE-treated pooled urine samples were mixed with SPE-treated 100 ng/mL standard in the 1:1 ratio. For high polyamine concentration, QC working solution, the SPE-treated pooled urine sample was mixed with SPE-treated 1,000 ng/mL standard in the 1:1 ratio.

Stability Studies

For stability study, Häkkinen et al. had previously demonstrated that both the standard mixtures and QC samples were stable after storing at six hours at room temperature (short-term stability), after storage at −20° C. and −80° C. respectively for two months (long-term stability) and after going three cycles of freezing and thawing before sample preparation (freeze thaw stability). For further verification, the content of polyamines and creatinine inside both standards and selected urine samples was analyzed. It was found that, upon five cycles of freeze and thaw, all the contents were still stable in six months' time when storing at −20° C. For the SPE-treated samples, it was stable for at least two days when storing at 4° C. and up to a year when storing at −20° C.

Instrumentation and Statistical Analysis

The quantitation of polyamines was performed by Ultra-high Performance Liquid Chromatography coupled with a triple quadrupole mass spectrometer (UPLC-MS/MS). LC separation was done by an Agilent 1290 Infinity Quaternary LC System while mass analyzing was done by an Agilent 6460 Triple Quadrupole mass spectrometer equipped with an Agilent Jet Stream technology electrospray ionization source. The column used was an Agilent EclipsePlus C18 RRHD (2.1×50 mm, 1.8 µm) protected with an Agilent SB-C18 guard column (2.1×5 mm, 1.8 µm).

The LC elution profiles were optimized as follows: Eluent A was water with 0.1% HFBA while eluent B was acetonitrile with 0.1% HFBA. Eluent A was decreased from 95% to 60% in 10 minutes. The gradient was then decreased from 60% to 10% of eluent A in 1 minute. Afterwards the gradient was held constant for 5 minutes. The gradient was then increased from 10% to 95% in 1 minute, followed by being held constant for 8 minutes. (Total run-time=25 minutes).

Autosampler and column temperature were set as 4° C. and 35° C. respectively. Injection was achieved by 5-second needle wash in Flush Port mode for 3 times with eluent B. In each time 10 µL was injected.

For the source parameter, drying gas (nitrogen) temperature was set as 300° C. with 5 l/min flow rate. Nebulizer pressure was 45 psi. Sheath gas temperature was set as 250° C. with 11 l/min flow rate. Capillary voltage was set as 3,500 V. For mass detection, scheduled multiple reaction monitoring (MRM) was performed. The information of MRM transitions can be found in Table 2.

TABLE 2

MRM transitions, dwell time, fragmentor, collision energy and cell accelerator voltage for Put, Spm, Spd and their corresponding internal standards

| | Precusor ion | Daughter ion | Dwell time (ms) | Fragmentor (V) | Collision energy (V) | Cell Accelerator Voltage (V) |
|---|---|---|---|---|---|---|
| Putrescine | 89 | 72* | 100 | 70 | 6 | 3 |
| Putrescine-d$_8$ | 97 | 80* | 100 | 70 | 6 | 3 |
| Spermidine | 146 | 112 | 100 | 90 | 10 | 3 |
| | 146 | 72* | 100 | 90 | 15 | 3 |
| Spermidine-d$_8$ | 154 | 120 | 100 | 90 | 10 | 3 |
| | 154 | 80* | 100 | 90 | 15 | 3 |
| Spermine | 203 | 129 | 100 | 90 | 10 | 3 |
| | 203 | 112* | 100 | 90 | 15 | 3 |
| Spermine-d$_8$ | 211 | 137 | 100 | 90 | 10 | 3 |
| | 211 | 120* | 100 | 90 | 15 | 3 |

(*Denoted the quantifier transitions).

The result was calculated using Agilent MassHunter Workstation software. Calibration curves were fitted linearly without any weighing. The correlation coefficients should not be smaller than 0.995. Acceptance values for each calibration points and quality control working solutions were ±30% to ensure accuracy. For precision verification, after every 10-sample injection each time, a 250 ng/mL standard was injected and checked if it can be reproduced (±15%).

For statistical analysis, the receiver operating characteristics (ROC) curve and the area under curve (AUC) were obtained by using GraphPad Prism 6 (GraphPad Software, San Diego, Calif., USA). A p value smaller than 0.05 (two-tailed) was considered as statistically significant during comparison based on Student's t-test.

Results

Urinary Polyamines Content

Figure 5A:
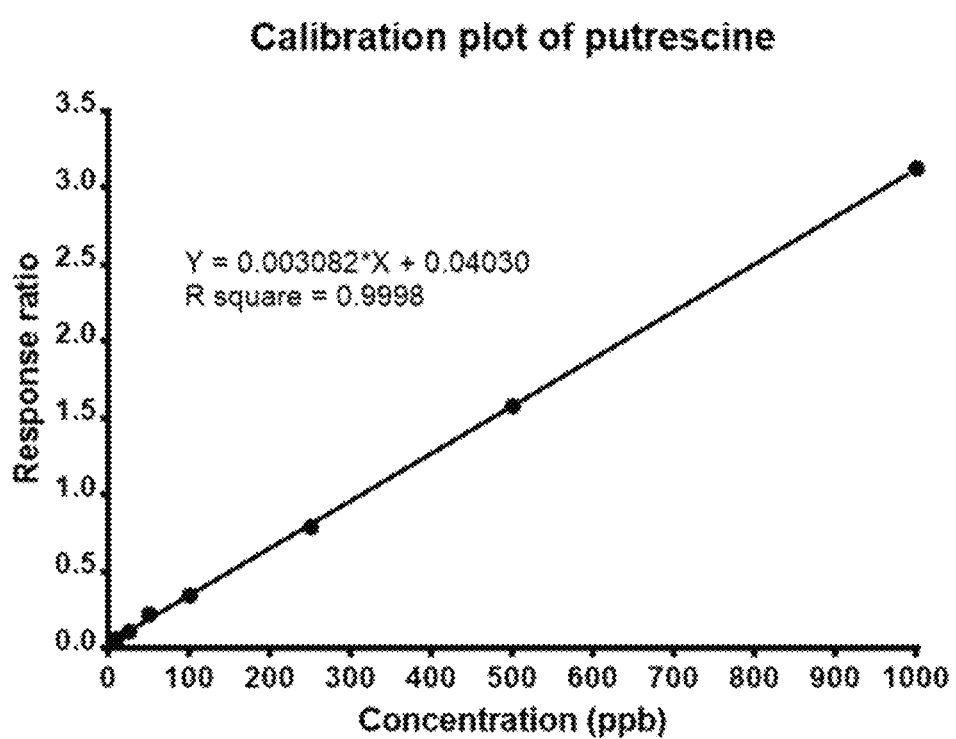
FIG. 5A shows the calibration graph for Put ($r^2$=0.9996).
Figure 5B:
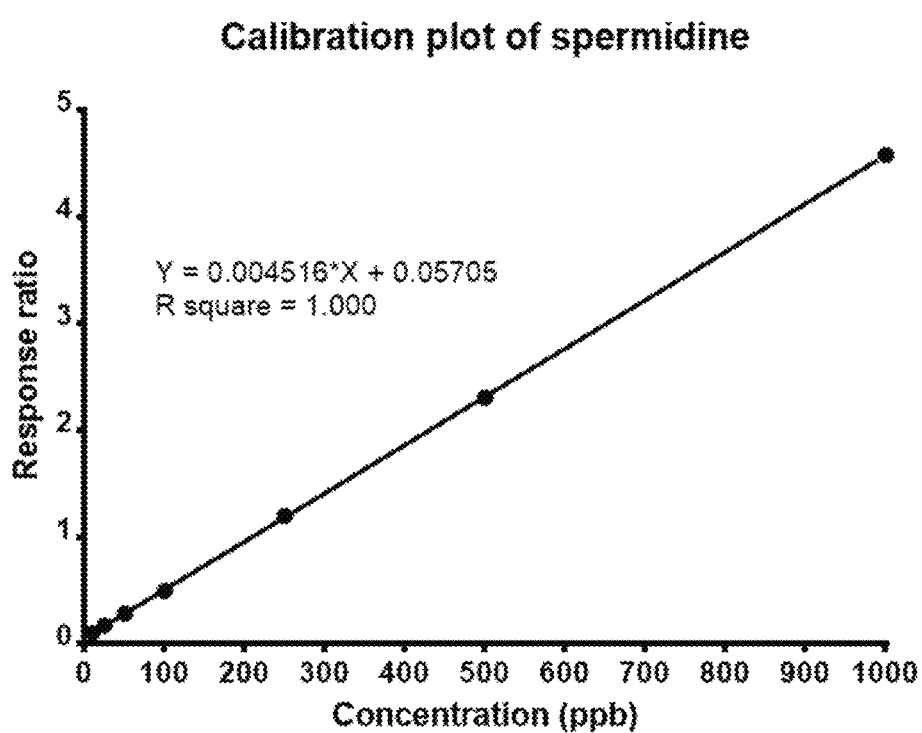
FIG. 5B shows the calibration graph for Spd ($r^2$=0.9993).
Figure 5C:
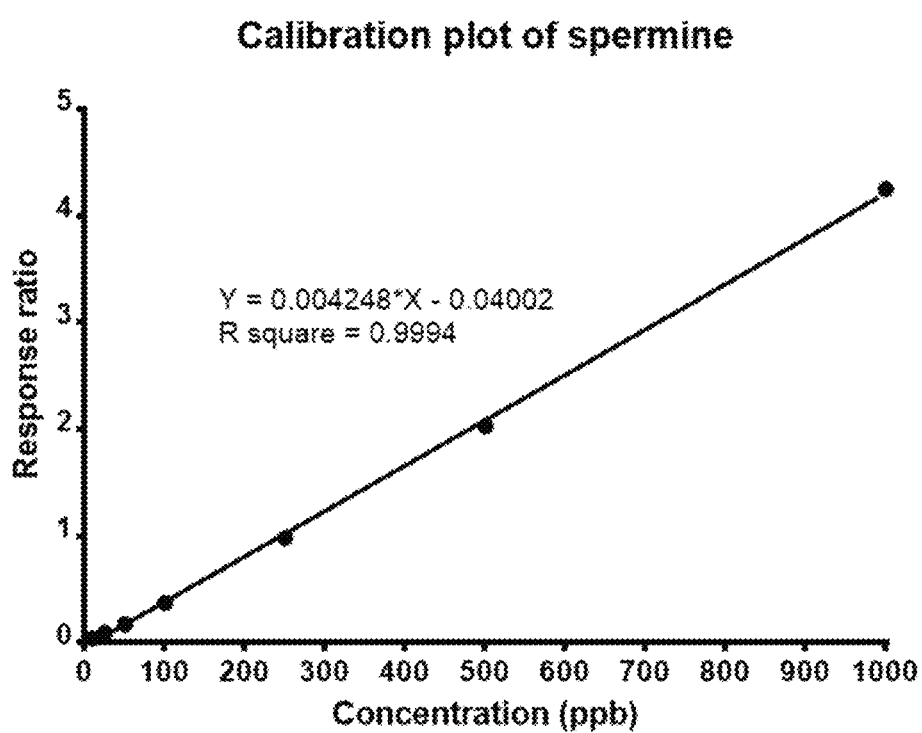
FIG. 5C shows the calibration graph for Spm ($r^2$=0.9995).

Put, Spd, Spm and their corresponding deuterated internal standards were successfully separated and quantified from all samples by UPLC-MS/MS. (FIG. 1) The calibration curves were all satisfactory with $r^2$ not less than 0.995 (FIG. 5A-FIG. 5C), and all QC measures passed which guaranteed the comparability between samples analyzed on different days. The mean urinary polyamines concentration for each patient was then normalized to their urinary creatinine levels and expressed as μmol/g of creatinine. (See Table 3 for creatinine results) This is to compensate for any diuresis processes hindering actual quantity measurements with reference to *Jung K Enzyme activities in urine: how should we express their excretion? A critical literature review. Eur J Clin Chem Clin Biochem.* 1991; 29:725-9.

TABLE 3

Summary of creatinine results from all patients

| Creatinine (ppm) | PCa (n = 66) | BPH (n = 88) | Healthy control (n = 11) | p value (PCa vs BPH) | p value (PCa vs HF) | p value (BPH vs HF) |
|---|---|---|---|---|---|---|
| Mean (SEM) | 828.30 (76.82) | 970.40 (69.06) | 1143 (269.40) | 0.173 | 0.151 | 0.427 |
| Median | 671.31 | 751.80 | 951.98 | | | |
| Range | 119.57-3102.61 | 171.43-3025.24 | 174.16-3183.77 | | | |

Figure 2A:
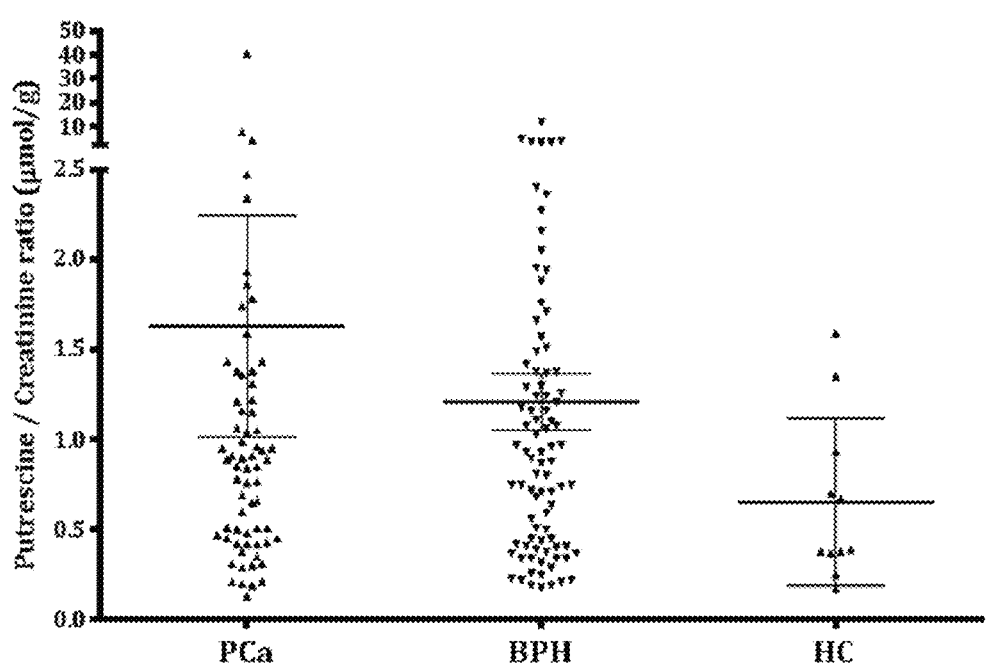
FIG. 2A shows the distribution of normalized Put values in PCa, BPH and HC.
Figure 2B:
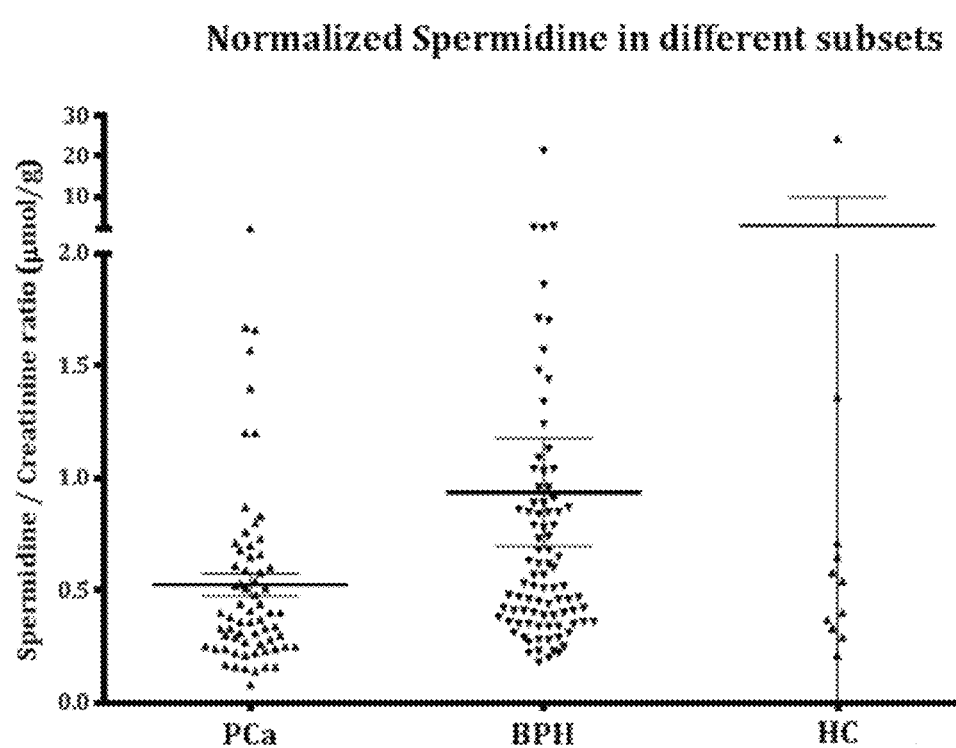
FIG. 2B shows the distribution of normalized Spd values in PCa, BPH and HC.
Figure 2C:
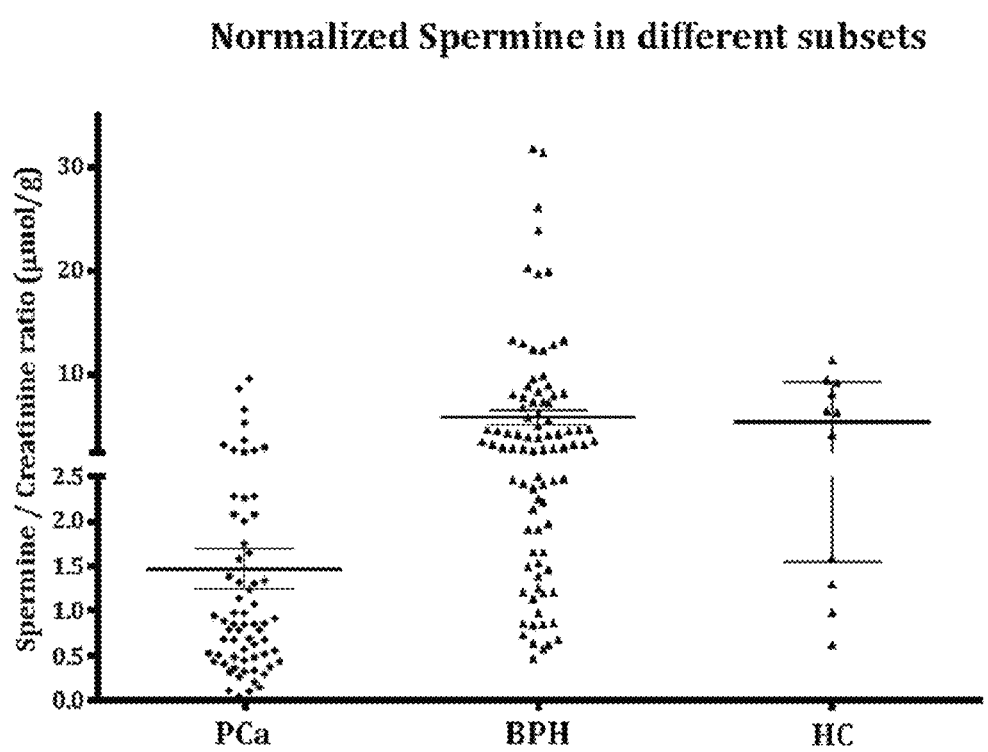
FIG. 2C shows the distribution of normalized Spm values in PCa, BPH and HC.

Table 4 and FIG. 2A to FIG. 2C show the data and graphical comparison of different subsets' normalized polyamines levels:

TABLE 4

Column statistics of normalized polyamine contents in different subsets. SEM represents the standard error of the mean.

| | PCa | BPH | HC | p value (PCa vs BPH) | p value (PCa vs HC) | p value (BPH vs HC) |
|---|---|---|---|---|---|---|
| Normalized Put | | | | | | |
| Mean (SEM) | 1.63 (0.61) | 1.21 (0.16) | 0.65 (0.14) | 0.459 | 0.522 | 0.212 |
| Median | 0.87 | 0.92 | 0.39 | | | |
| Range | 0.13-40.64 | 0.18-12.04 | 0.17-1.59 | | | |
| 25% Percentile | 0.45 | 0.41 | 0.37 | | | |
| 75% Percentile | 1.24 | 1.38 | 0.93 | | | |

TABLE 4-continued

Column statistics of normalized polyamine contents in different subsets. SEM represents the standard error of the mean.

|  | PCa | BPH | HC | p value (PCa vs BPH) | p value (PCa vs HC) | p value (BPH vs HC) |
|---|---|---|---|---|---|---|
| Normalized Spd | | | | | | |
| Mean (SEM) | 0.52 (0.05) | 0.94 (0.24) | 2.71 (2.17) | 0.147 | 0.014 | 0.081 |
| Median | 0.39 | 0.52 | 0.54 | | | |
| Range | 0.08-2.09 | 0.18-21.42 | 0.21-24.40 | | | |
| 25% Percentile | 0.25 | 0.36 | 0.33 | | | |
| 75% Percentile | 0.65 | 0.89 | 0.71 | | | |
| Normalized Spm | | | | | | |
| Mean (SEM) | 1.47 (0.22) | 5.87 (0.71) | 5.43 (1.17) | <0.0001 | <0.0001 | 0.833 |
| Median | 0.86 | 3.25 | 6.37 | | | |
| Range | 0.05-9.57 | 0.47-31.78 | 0.63-11.36 | | | |
| 25% Percentile | 0.48 | 1.72 | 1.30 | | | |
| 75% Percentile | 1.82 | 7.65 | 9.18 | | | |

The black bar in FIG. 2A to FIG. 2C indicates the mean value of each subset while the error bar indicates the corresponding SEM.

Among the three polyamines monitored, normalized Spm showed a significant decrease in PCa patients compared to non-cancerous cases including BPH patients and HC in terms of statistical means (Unpaired student's t-test). In detail, the mean value was 1.47 in PCa vs 5.87 in BPH vs 5.43 in HC. p values were <0.0001 in t-test, which means significant differences at the pre-set criteria of $p<0.05$. For normalized Put and Spd, no obvious enhancement or suppression could be observed by looking at their distributions or comparing their mean values by t-test. (Put: 1.63 in PCa vs 1.21 in BPH vs 0.65 in HC; Spd: 0.52 in PCa vs 0.94 in BPH vs 2.71 in HC).

Receiver Operating Characteristics Analysis

Figure 3:
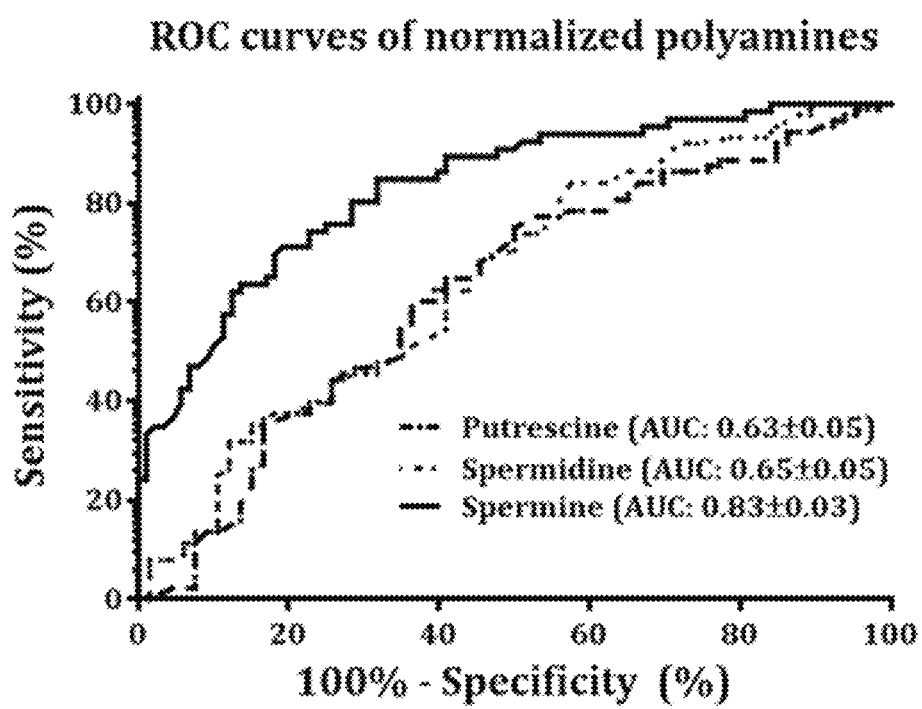
FIG. 3 shows the receiver operating characteristic analysis for normalized Put, Spd and Spm values.

FIG. 3 shows the ROC curves of the three normalized polyamines for evaluating the diagnostic power of the shortlisted polyamines for PCa diagnosis. The AUC for normalized Put, Spd and Spm were found to be 0.63±0.05, 0.65±0.05 and 0.83±0.03 respectively. The threshold values for Spm with the corresponding sensitivity and specificity were listed in Table 5.

TABLE 5

Sensitivity and Specificity for normalized Spm at different threshold values.

| Threshold | Sensitivity (%) | 95% CI | Specificity (%) | 95% CI |
|---|---|---|---|---|
| <0.0800 | 1.515 | 0.03835% to 8.155% | 100. | 96.34% to 100.0% |
| <0.1150 | 3.03 | 0.3691% to 10.52% | 100 | 96.34% to 100.0% |
| <0.1350 | 4.545 | 0.9474% to 12.71% | 100 | 96.34% to 100.0% |
| <0.1800 | 6.061 | 1.676% to 14.80% | 100 | 96.34% to 100.0% |
| <0.2400 | 7.576 | 2.506% to 16.80% | 100 | 96.34% to 100.0% |
| <0.2900 | 9.091 | 3.410% to 18.74% | 100 | 96.34% to 100.0% |
| <0.3150 | 10.61 | 4.372% to 20.64% | 100 | 96.34% to 100.0% |
| <0.3250 | 12.12 | 5.381% to 22.49% | 100 | 96.34% to 100.0% |
| <0.3350 | 13.64 | 6.430% to 24.31% | 100 | 96.34% to 100.0% |
| <0.3550 | 15.15 | 7.512% to 26.10% | 100 | 96.34% to 100.0% |
| <0.3750 | 16.67 | 8.625% to 27.87% | 100 | 96.34% to 100.0% |
| <0.4000 | 18.18 | 9.763% to 29.61% | 100 | 96.34% to 100.0% |
| <0.4300 | 19.7 | 10.93% to 31.32% | 100 | 96.34% to 100.0% |
| <0.4450 | 22.73 | 13.31% to 34.70% | 100 | 96.34% to 100.0% |
| <0.4600 | 24.24 | 14.54% to 36.36% | 100 | 96.34% to 100.0% |
| <0.4800 | 24.24 | 14.54% to 36.36% | 98.99 | 94.50% to 99.97% |
| <0.5000 | 27.27 | 17.03% to 39.64% | 98.99 | 94.50% to 99.97% |
| <0.5200 | 28.79 | 18.30% to 41.25% | 98.99 | 94.50% to 99.97% |
| <0.5350 | 30.3 | 19.59% to 42.85% | 98.99 | 94.50% to 99.97% |
| <0.5500 | 31.82 | 20.89% to 44.44% | 98.99 | 94.50% to 99.97% |
| <0.5700 | 33.33 | 22.20% to 46.01% | 98.99 | 94.50% to 99.97% |
| <0.6050 | 34.85 | 23.53% to 47.58% | 97.98 | 92.89% to 99.75% |
| <0.6350 | 34.85 | 23.53% to 47.58% | 95.96 | 89.98% to 98.89% |
| <0.6600 | 36.36 | 24.87% to 49.13% | 94.95 | 88.61% to 98.34% |
| <0.6850 | 39.39 | 27.58% to 52.19% | 93.94 | 87.27% to 97.74% |
| <0.6950 | 40.91 | 28.95% to 53.71% | 93.94 | 87.27% to 97.74% |
| <0.7200 | 42.42 | 30.34% to 55.21% | 93.94 | 87.27% to 97.74% |
| <0.7650 | 42.42 | 30.34% to 55.21% | 92.93 | 85.97% to 97.11% |
| <0.7950 | 45.45 | 33.14% to 58.19% | 92.93 | 85.97% to 97.11% |

TABLE 5-continued

Sensitivity and Specificity for normalized Spm at different threshold values.

| Threshold | Sensitivity (%) | 95% CI | Specificity (%) | 95% CI |
|---|---|---|---|---|
| <0.8200 | 46.97 | 34.56% to 59.66% | 92.93 | 85.97% to 97.11% |
| <0.8450 | 46.97 | 34.56% to 59.66% | 91.92 | 84.70% to 96.45% |
| <0.8550 | 48.48 | 35.99% to 61.12% | 90.91 | 83.44% to 95.76% |
| <0.8650 | 51.52 | 38.88% to 64.01% | 89.9 | 82.21% to 95.05% |
| <0.8800 | 53.03 | 40.34% to 65.44% | 88.89 | 80.99% to 94.32% |
| <0.9100 | 54.55 | 41.81% to 66.86% | 88.89 | 80.99% to 94.32% |
| <0.9400 | 56.06 | 43.30% to 68.26% | 88.89 | 80.99% to 94.32% |
| <0.9650 | 57.58 | 44.79% to 69.66% | 88.89 | 80.99% to 94.32% |
| <0.9850 | 57.58 | 44.79% to 69.66% | 87.88 | 79.78% to 93.58% |
| <1.035 | 60.61 | 47.81% to 72.42% | 86.87 | 78.59% to 92.82% |
| <1.110 | 62.12 | 49.34% to 73.78% | 86.87 | 78.59% to 92.82% |
| <1.145 | 62.12 | 49.34% to 73.78% | 85.86 | 77.41% to 92.05% |
| <1.175 | 63.64 | 50.87% to 75.13% | 85.86 | 77.41% to 92.05% |
| <1.205 | 63.64 | 50.87% to 75.13% | 84.85 | 76.24% to 91.26% |
| <1.225 | 63.64 | 50.87% to 75.13% | 82.83 | 73.94% to 89.67% |
| <1.250 | 65.15 | 52.42% to 76.47% | 82.83 | 73.94% to 89.67% |
| <1.280 | 65.15 | 52.42% to 76.47% | 81.82 | 72.80% to 88.85% |
| <1.305 | 65.15 | 52.42% to 76.47% | 80.81 | 71.66% to 88.03% |
| <1.320 | 66.67 | 53.99% to 77.80% | 80.81 | 71.66% to 88.03% |
| <1.335 | 68.18 | 55.56% to 79.11% | 80.81 | 71.66% to 88.03% |
| <1.365 | 69.7 | 57.15% to 80.41% | 80.81 | 71.66% to 88.03% |
| <1.425 | 71.21 | 58.75% to 81.70% | 79.8 | 70.54% to 87.20% |
| <1.480 | 71.21 | 58.75% to 81.70% | 78.79 | 69.42% to 86.36% |
| <1.520 | 71.21 | 58.75% to 81.70% | 77.78 | 68.31% to 85.52% |
| <1.560 | 71.21 | 58.75% to 81.70% | 76.77 | 67.21% to 84.67% |
| <1.585 | 72.73 | 60.36% to 82.97% | 76.77 | 67.21% to 84.67% |
| <1.620 | 72.73 | 60.36% to 82.97% | 75.76 | 66.11% to 83.81% |
| <1.655 | 74.24 | 61.99% to 84.22% | 75.76 | 66.11% to 83.81% |
| <1.705 | 74.24 | 61.99% to 84.22% | 73.74 | 63.93% to 82.07% |
| <1.830 | 75.76 | 63.64% to 85.46% | 73.74 | 63.93% to 82.07% |
| <1.940 | 75.76 | 63.64% to 85.46% | 71.72 | 61.78% to 80.31% |
| <1.990 | 75.76 | 63.64% to 85.46% | 70.71 | 60.71% to 79.43% |
| <2.045 | 77.27 | 65.30% to 86.69% | 70.71 | 60.71% to 79.43% |
| <2.105 | 80.3 | 68.68% to 89.07% | 70.71 | 60.71% to 79.43% |
| <2.175 | 80.3 | 68.68% to 89.07% | 69.7 | 59.64% to 78.53% |
| <2.235 | 80.3 | 68.68% to 89.07% | 68.69 | 58.59% to 77.64% |
| <2.255 | 80.3 | 68.68% to 89.07% | 67.68 | 57.53% to 76.73% |
| <2.270 | 81.82 | 70.39% to 90.24% | 67.68 | 57.53% to 76.73% |
| <2.325 | 84.85 | 73.90% to 92.49% | 67.68 | 57.53% to 76.73% |
| <2.390 | 84.85 | 73.90% to 92.49% | 66.67 | 56.48% to 75.82% |
| <2.415 | 84.85 | 73.90% to 92.49% | 65.66 | 55.44% to 74.91% |
| <2.435 | 84.85 | 73.90% to 92.49% | 64.65 | 54.40% to 73.99% |
| <2.455 | 84.85 | 73.90% to 92.49% | 63.64 | 53.36% to 73.07% |
| <2.465 | 84.85 | 73.90% to 92.49% | 62.63 | 52.33% to 72.15% |
| <2.485 | 84.85 | 73.90% to 92.49% | 61.62 | 51.30% to 71.22% |
| <2.510 | 84.85 | 73.90% to 92.49% | 60.61 | 50.28% to 70.28% |
| <2.585 | 86.36 | 75.69% to 93.57% | 60.61 | 50.28% to 70.28% |
| <2.665 | 86.36 | 75.69% to 93.57% | 59.6 | 49.26% to 69.34% |
| <2.715 | 87.88 | 77.51% to 94.62% | 59.6 | 49.26% to 69.34% |
| <2.770 | 89.39 | 79.36% to 95.63% | 59.6 | 49.26% to 69.34% |
| <2.800 | 89.39 | 79.36% to 95.63% | 58.59 | 48.24% to 68.40% |
| <2.820 | 89.39 | 79.36% to 95.63% | 57.58 | 47.23% to 67.45% |
| <2.845 | 89.39 | 79.36% to 95.63% | 56.57 | 46.23% to 66.50% |
| <2.895 | 89.39 | 79.36% to 95.63% | 55.56 | 45.22% to 65.55% |
| <2.935 | 89.39 | 79.36% to 95.63% | 54.55 | 44.22% to 64.59% |
| <2.965 | 89.39 | 79.36% to 95.63% | 53.54 | 43.23% to 63.62% |
| <3.110 | 90.91 | 81.26% to 96.59% | 53.54 | 43.23% to 63.62% |
| <3.235 | 90.91 | 81.26% to 96.59% | 52.53 | 42.24% to 62.66% |
| <3.245 | 90.91 | 81.26% to 96.59% | 51.52 | 41.25% to 61.68% |
| <3.380 | 92.42 | 83.20% to 97.49% | 50.51 | 40.27% to 60.71% |
| <3.555 | 92.42 | 83.20% to 97.49% | 49.49 | 39.29% to 59.73% |
| <3.625 | 92.42 | 83.20% to 97.49% | 48.48 | 38.32% to 58.75% |
| <3.760 | 93.94 | 85.20% to 98.32% | 48.48 | 38.32% to 58.75% |
| <3.920 | 93.94 | 85.20% to 98.32% | 47.47 | 37.34% to 57.76% |
| <4.055 | 93.94 | 85.20% to 98.32% | 46.46 | 36.38% to 56.77% |
| <4.170 | 93.94 | 85.20% to 98.32% | 45.45 | 35.41% to 55.78% |
| <4.205 | 93.94 | 85.20% to 98.32% | 44.44 | 34.45% to 54.78% |
| <4.235 | 93.94 | 85.20% to 98.32% | 43.43 | 33.50% to 53.77% |
| <4.290 | 93.94 | 85.20% to 98.32% | 42.42 | 32.55% to 52.77% |
| <4.430 | 93.94 | 85.20% to 98.32% | 41.41 | 31.60% to 51.76% |
| <4.560 | 93.94 | 85.20% to 98.32% | 40.4 | 30.66% to 50.74% |
| <4.595 | 93.94 | 85.20% to 98.32% | 39.39 | 29.72% to 49.72% |
| <4.625 | 93.94 | 85.20% to 98.32% | 38.38 | 28.78% to 48.70% |
| <4.695 | 93.94 | 85.20% to 98.32% | 37.37 | 27.85% to 47.67% |
| <4.880 | 93.94 | 85.20% to 98.32% | 36.36 | 26.93% to 46.64% |

TABLE 5-continued

Sensitivity and Specificity for normalized Spm at different threshold values.

| Threshold | Sensitivity (%) | 95% CI | Specificity (%) | 95% CI |
|---|---|---|---|---|
| <5.180 | 93.94 | 85.20% to 98.32% | 35.35 | 26.01% to 45.60% |
| <5.440 | 95.45 | 87.29% to 99.05% | 35.35 | 26.01% to 45.60% |
| <5.700 | 95.45 | 87.29% to 99.05% | 34.34 | 25.09% to 44.56% |
| <6.055 | 95.45 | 87.29% to 99.05% | 33.33 | 24.18% to 43.52% |
| <6.305 | 95.45 | 87.29% to 99.05% | 32.32 | 23.27% to 42.47% |
| <6.435 | 95.45 | 87.29% to 99.05% | 31.31 | 22.36% to 41.41% |
| <6.555 | 95.45 | 87.29% to 99.05% | 30.3 | 21.47% to 40.36% |
| <6.685 | 96.97 | 89.48% to 99.63% | 30.3 | 21.47% to 40.36% |
| <7.000 | 96.97 | 89.48% to 99.63% | 29.29 | 20.57% to 39.29% |
| <7.270 | 96.97 | 89.48% to 99.63% | 28.28 | 19.69% to 38.22% |
| <7.310 | 96.97 | 89.48% to 99.63% | 27.27 | 18.80% to 37.15% |
| <7.540 | 96.97 | 89.48% to 99.63% | 26.26 | 17.93% to 36.07% |
| <7.885 | 96.97 | 89.48% to 99.63% | 25.25 | 17.06% to 34.98% |
| <8.060 | 96.97 | 89.48% to 99.63% | 24.24 | 16.19% to 33.89% |
| <8.130 | 96.97 | 89.48% to 99.63% | 23.23 | 15.33% to 32.79% |
| <8.245 | 96.97 | 89.48% to 99.63% | 21.21 | 13.64% to 30.58% |
| <8.495 | 96.97 | 89.48% to 99.63% | 20.2 | 12.80% to 29.46% |
| <8.755 | 98.48 | 91.84% to 99.96% | 20.2 | 12.80% to 29.46% |
| <8.880 | 98.48 | 91.84% to 99.96% | 19.19 | 11.97% to 28.34% |
| <9.040 | 98.48 | 91.84% to 99.96% | 18.18 | 11.15% to 27.20% |
| <9.335 | 98.48 | 91.84% to 99.96% | 17.17 | 10.33% to 26.06% |
| <9.520 | 98.48 | 91.84% to 99.96% | 16.16 | 9.530% to 24.91% |
| <9.560 | 98.48 | 91.84% to 99.96% | 15.15 | 8.736% to 23.76% |
| <9.700 | 100 | 94.56% to 100.0% | 15.15 | 8.736% to 23.76% |
| <10.60 | 100 | 94.56% to 100.0% | 14.14 | 7.953% to 22.59% |
| <11.85 | 100 | 94.56% to 100.0% | 13.13 | 7.181% to 21.41% |
| <12.38 | 100 | 94.56% to 100.0% | 12.12 | 6.423% to 20.22% |
| <12.63 | 100 | 94.56% to 100.0% | 11.11 | 5.679% to 19.01% |
| <12.93 | 100 | 94.56% to 100.0% | 10.1 | 4.951% to 17.79% |
| <13.15 | 100 | 94.56% to 100.0% | 9.091 | 4.242% to 16.56% |
| <13.29 | 100 | 94.56% to 100.0% | 8.081 | 3.553% to 15.30% |
| <16.50 | 100 | 94.56% to 100.0% | 7.071 | 2.890% to 14.03% |
| <19.83 | 100 | 94.56% to 100.0% | 6.061 | 2.256% to 12.73% |
| <20.11 | 100 | 94.56% to 100.0% | 5.051 | 1.660% to 11.39% |
| <22.08 | 100 | 94.56% to 100.0% | 4.04 | 1.112% to 10.02% |
| <25.01 | 100 | 94.56% to 100.0% | 3.03 | 0.6293% to 8.601% |
| <28.75 | 100 | 94.56% to 100.0% | 2.02 | 0.2456% to 7.108% |
| <31.57 | 100 | 94.56% to 100.0% | 1.01 | 0.02557% to 5.500% |

The relationship between polyamines and cancer has long been investigated by scientists. It is generally believed that increase of polyamine levels in blood or urine reflect the enhanced levels of polyamine synthesis in rapid-growing cancer tissues/cells, since they are associated with increased cell proliferation, decreased apoptosis and increased expression of genes affecting tumor invasion and metastasis.

In Russell D H. *Increased polyamine concentrations in the urine of human cancer patients. Nat New Biol.* 1971; 233(39):144-5 firstly reported the increase of urinary polyamines levels in various solid tumors, including ovarian teratoma, rectal carcinoma, lymphosarcoma, osteogenic sarcoma and acute myelocytic leukaemia. Kyoko Hiramatsu et al. $N^1,N^{12}$-*Diacetylspermine as a Sensitive and Specific Novel Marker for Early-and Late-Stage Colorectal and Breast Cancers. Clin Cancer Res.* 2005; 11(8):2986-90 reported an increase in $N^1, N^{12}$-Diacetylspermine in patients with early and late stage colorectal and breast cancers and established its role to be a novel marker for these cancers. In cases of cervical cancer, Lee et al. *Altered urinary profiles of polyamines and endogenous steroids in patients with benign cervical disease and cervical cancer. Cancer Lett.* 2003; 201(2):121-31 had shown a significant elevation in polyamines level in Put, Spd and Spm. For hepatic cancer, Liu et al. *Determination of polyamine metabolome in plasma and urine by ultrahigh performance liquid chromatography-tandem mass spectrometry method: Application to identify potential markers for human hepatic cancer. Anal Chim Acta.* 2013; 791:36-45 monitored the level differences between polyamines, polyamine precursors and catabolites in both patients' plasma and urines. By analyzing these results carefully, indeed it could be observed that different kinds of polyamines showed different variations depending on the type of cancers. The claim of urinary polyamine levels elevating in cancer cases is not specific enough.

Nevertheless, very few reports focused on detecting the effects of PCa on urinary polyamines levels, which in turn might provide a potential diagnostic tool for this increasing common cancer. In 1975 Fair et al. *Urinary polyamine levels in the diagnosis of carcinoma of the prostate. J Urol.* 1975; 114(1):88-92 had reported a significant elevation of urinary Spd content in PCa patients by electrophoresis, but not Put and Spm. Horn et al. *Relationship of urinary polyamines to tumor activity and tumor volume in patients. Cancer Res.* 1984; 44(10):4675-8 analyzed urinary Spd and Put content from patients with tumors in either breast, stomach, prostate, female genital tract, or metastatic carcinomas of unknown origins by LC with fluorometric detector in 1984 yielding an indeterminant conclusion. With the advance of analytical field, in the current disclosure, the potential abilities of three natural polyamines: Put, Spd and Spm, as urinary biomarkers for screening of PCa were evaluated by UPLC-MS/MS. Through a well validated method using separate deuterated internal standards for correcting matrix effects for each polyamine, it is believed that the analytical performance was much more reliable.

The observation of a declined level in urinary Spm actually was reasonable from results of previous literatures about PCa studies. Although only a limited number of tissue specimens had been examined, van der Graaf et al. *Proton MR spectroscopy of prostatic tissue focused on the detection of spermine, a possible biomarker of malignant behavior in prostate cancer MAGMA* 2000; 10(3):153-9 reported a reduced Spm content in tumor prostatic tissues compared to normal and benign hyperplastic prostatic tissues by high performance liquid chromatography with fluorometric detector. Swanson et al. *Proton HR-MAS spectroscopy and quantitative pathologic analysis of MRI/3D-MRSI-targeted postsurgical prostate tissues. Magn Reson Med.* 2003; 50(5): 944-54 also reported a decreased Spm level in prostate tissue samples by Proton high-resolution magic angle spinning nuclear magnetic resonance spectroscopy and quantitative histopathology. High grade cancer prostate tissue could be distinguished from low grade cancer tissue by decreased concentrations of Spm and citrate, as reported by GF Giskeødegård et al *Spermine and citrate as metabolic biomarkers for assessing prostate cancer aggressiveness. PLoS One* 2013; 8(4):e62375. Apart from direct monitoring of prostate tissue, Serkova et al. *The metabolites citrate, myo-inositol, and spermine are potential age-independent markers of prostate cancer in human expressed prostatic secretions. Prostate.* 2008; 68(6), 620-8 reported that in human expressed prostatic secretions, citrate, myo-inositol and Spm are potentially important markers of PCa, and all of them showed a decreased level in PCa patients compared to control samples. With respect to these previous research projects, a decrease in urinary Spm content could be foreseen, because urine represents a fluid closely related to exfoliated cancer cells and secreted prostatic products from the prostate. In essence, urine has the advantages of ready availability and the collection of which is non-invasive. Therefore the discovery of a useful urine PCa biomarker is inspiring to the current medical situation for reducing unnecessary biopsies and arranging patients for appropriate therapies.

Figure 4:
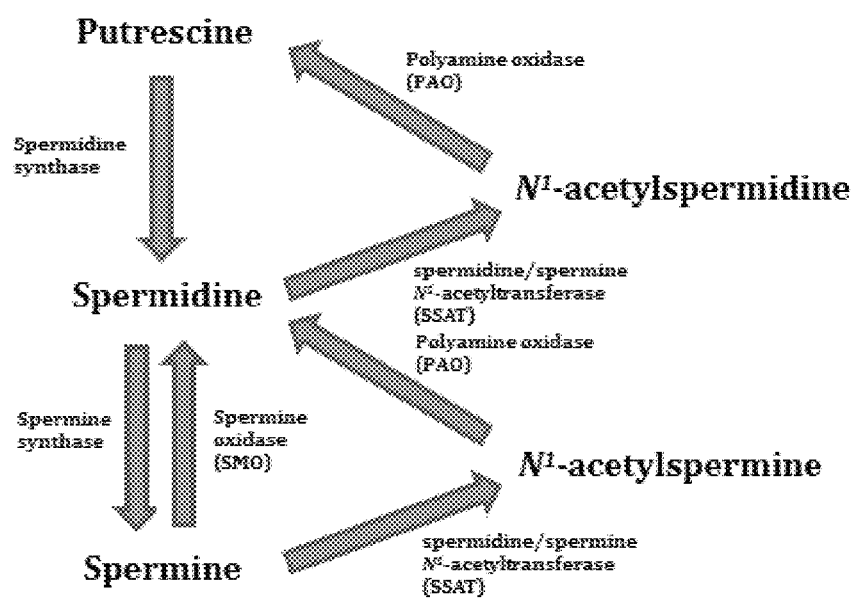
FIG. 4 shows the polyamine metabolic pathway (focusing on Put, Spd and Spm only).

To explain the declined level of Spm in PCa patients, the exact mechanisms lack clear evidence and are still under research. Schipper et al. *Polyamines and prostatic cancer Biochem Soc Trans.* 2003; 31(2):375-80 suggested a possible explanation that changes of cell organization caused by cancer cell proliferation finally result in a decreased luminal volume, which in turn reduces the amount of secreted compounds in prostate tissue, prostatic fluid or even urine. But this could hardly explain why only urinary Spm level declined. Leo et al. *Non-destructive quantitation of spermine in human prostate tissue samples using HRMAS 1H NMR spectroscopy at 9.4 T FEBS Letters.* 2001; 494(1-2):112-6 reported that Spm was a proposed endogenous inhibitor to prostate cancer growth, and a linear correlation was found between Spm content and the volume percentage of normal prostatic epithelial cells as quantified by histopathology. And in recent studies it was suggested that dysregulation of polyamine metabolism, or more specifically polyamine catabolism, may be involved in carcinogenesis. Increases in spermine oxidase (SMO) and spermidine/spermine $N^1$-acetyltransferase (SSAT) expression were observed in both precursor prostatic inflammatory atrophy lesions and early prostatic intraepithelial neoplastic lesions, which resulted in a depletion of Spm content (FIG. 4).

This hypothesis is also supported by the observation of a significant increase in urinary diacetylspermine content in patients with urogenital malignancies resulted from the enzymatic action of SSAT, as reported by Hiramatsu, et al. *Diagnostic and prognostic usefulness of $N^1$, $N^8$-diacetylspermidine and $N^1$, $N^{12}$-diacetylspermine in urine as novel markers of malignancy. J Cancer Res Clin Oncol.* 1997; 123(10):539-45. Therefore the observation of a decrease in urinary Spm, as described herein, is in line with previous findings and suggested mechanisms. Without being bound by theory, it is hypothesized that the action of SMO and SSAT counteracted each other so no significant changes were found for Spd.

Nevertheless, unlike what GF Giskeødegård et al. *Spermine and citrate as metabolic biomarkers for assessing prostate cancer aggressiveness. PLoS One* 2013; 8(4): e62375 reported that prostatic Spin content can act as a biomarker to assess PCa aggressiveness, determinant definitive conclusion on whether urinary Spm shows similar cancer grade-differentiating ability could be established from the data disclosed herein. From the results, a drop in high grade cancer (GS=8-10) was observed comparing with low grade cancer (GS≤6), albeit not that significant. (1.23 in High grade vs 1.47 in low grade; p=0.611) Instead, it acts like a diagnostic biomarker working in accordance with TRUSPB for PCa diagnosis.

Figure 6:
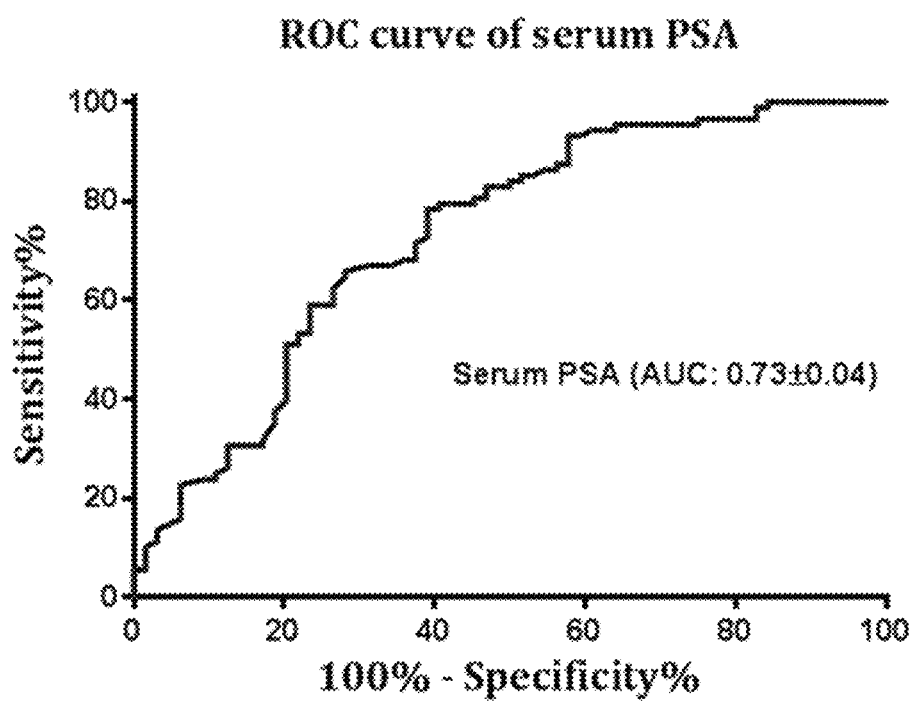
FIG. 6 shows the receiver operating characteristics curve for serum PSA test.

The PSA test leaves much to be desired as a primary screening test. It has been shown to cause over-diagnosis especially in patients showing values in the grey zone. For example, serum PSA alone demonstrated fair sensitivity and specificity of 65% and 47% respectively. Li et al. *Macrophage inhibitory cytokine 1 biomarker serum immunoassay in combination with PSA is a more specific diagnostic tool for detection of prostate cancer PLoS One.* 2015; 10(4): e0122249 reported an even poorer sensitivity and specificity for it in their study (Sensitivity=54.8%, Specificity=57.1%, AUC=0.684). Another large-scale study by Ferro et al. *Prostate Health Index (Phi) and Prostate Cancer Antigen 3 (PCA3) significantly improve prostate cancer detection at initial biopsy in a total PSA range of 2-10 ng/mL. PLoS One* 2013; 8(7):e67687 showed that total PSA only gave AUC value of 0.52±0.07. When focusing on patients with PSA>4.0 ng/mL, the PSA test shows the best screening performance (AUC=0.73±0.04; See FIG. 6), but it is still poorer than that of urinary Spm testing methods described herein. Sensitivity and specificity were 67.05% and 68.75% respectively. Therefore urinary Spm is able to act as a secondary screening test to men with serum PSA>4.0 ng/mL to differentiate PCa and non-cancerous cases including BPH for supplementing PSA test.

To conclude on the basis of the first part of the present disclosure, the potential roles of the three main urinary polyamines as PCa biomarkers were evaluated. Among Put, Spd and Spm, Spm demonstrated an outstanding diagnostic performance for PCa, in particular for patients with elevated serum PSA level, upon comparison of their levels in PCa and BPH patients. Its AUC value is 0.83±0.03. This could help the current medical challenge brought by poor specificity of serum PSA test. And with our developed lanthanide based bioprobes, we can achieve a simple and quick quantification for PCa screening.

Provided herein is a method of detecting one or more urinary polyamines, comprising the steps of:
 a. providing a urine sample; and
 b. detecting the presence of the one or more urinary polyamines in the test sample.

In certain embodiments, the urinary polyamine is at least one of Put, Spm, and Spd.

The urine sample can be obtained from an individual. The individual can be any animal, such as a mammal, rodent, canine, feline, equine, bovine, porcine, primate (e.g. non-human primate), or human.

In certain embodiments, the sample is obtained from a human male. In certain embodiments, the human male has PSA greater than about 2.0 ng/mL, 3.0 ng/mL, 4.0 ng/mL, 5.0 ng/mL, 6.0 ng/mL, 7.0 ng/mL, 8.0 ng/mL, 9.0 ng/mL, or 10.0 ng/mL.

In certain embodiments, the human male has PSA in the range of about 2.0 ng/mL to about 10.0 ng/mL, about 3.0 ng/mL to about 10.0 ng/mL, or about 4.0 ng/mL to about 10.0 ng/mL.

The urine sample can optionally be pretreated, e.g., to remove potentially interfering analytes and/or proteins, as described herein in order to improve, e.g., accuracy, ease of handling, etc.

Any method useful for determining the amount of polyamines in a sample can be used to determine the one or more urinary polyamine levels. The selection of the appropriate method is well within the worker of ordinary skill. Methods for detecting and/or determining the levels of the one or more polyamines (e.g., spermine) include, but are not limited to, nuclear magnetic resonance (NMR), mass spectrometry (MS), high performance liquid chromatography (HPLC), ultra-performance liquid chromatography (UPLC), isocratic HPLC, gradient HPLC, normal-phase chromatography, reverse-phase HPLC, size exclusion chromatography, ion exchange chromatography, capillary electrophoresis, microfluidics, chromatography, gas chromatography (GC), thin-layer chromatography (TLC), immobilized metal ion affinity chromatography (IMAC), affinity chromatography, immunoassays, enzymatic approach, colorimetric assays, chemosensing using extended-gate organic field-effect transistor (OFET) sensors, chemosensing using semiconductor sensors, and gravimetric analysis.

In certain embodiments, the compound of Formula 1 and methods described herein are used to detect and/or determine the level of the one or more urinary polyamines (e.g., spermine).

In certain embodiments, the method for detecting the one or more urinary polyamines (e.g., spermine) involves the composition and methods described in U.S. non-provisional application Ser. No. 15/784,269, which discloses colorimetric methods for detecting spermine using lanthanide complexes and DNA capped gold nanoparticles.

The methods and compositions provided herein can also be used to detect spermine in samples obtained from individuals suspected of having breast cancer. In these embodiments, the sample can be a biopsy comprising breast tissue suspected of being cancerous. Accordingly, the methods and compositions described herein can be used in connection with the detection of spermine in breast tissue and determining the susceptibility of an individual to breast cancer.

The methods and compositions provided herein can also be used to detect any type of polyamine present in samples obtain from any possible source and is thus not limited to urine samples. The sample can be obtained from any source, for example, plants, soil, waste streams, water, soil, air, pharmaceutical, cosmetics, biological, chemical, meat, food, beverages, and the like.

The method of detecting one or more urinary polyamines can further comprise the step of comparing the concentration of spermine in the test sample with a reference concentration and determining whether the individual has an increased susceptibility to prostate cancer, wherein a decrease in the concentration of spermine in the test sample relative to the reference sample indicates an increased susceptibility to prostate cancer in the individual.

In certain embodiments, the concentration of spermine in the test sample, which indicates an increased susceptibility to prostate cancer in the individual is lower than about 1.8 ng/mL, about 1.7 ng/mL, about 1.6 ng/mL, about 1.5 ng/mL, about 1.4 ng/mL, about 1.3 ng/mL, about 1.2 ng/mL, about 1.1 ng/mL, or about 1.0 ng/mL.

In certain embodiments the concentration of spermine in the test sample, which indicates an increased susceptibility to prostate cancer in the individual is about 1.1 ng/mL to about 1.5 ng/mL or about 1.2 ng/mL to about 1.5 ng/mL.

In certain embodiments of the methods provided herein, an AUC probability value that is at least about 60% or higher is indicative of prostate cancer. The present disclosure contemplates methods wherein an AUC value is calculable, and thereby prediction of prostate cancer at a probability that is greater than about 61%, 62%, 63%, 64%, 65%, 66%, 67%, 68%, 69%, 70%, 71%, 72%, 73%, 73%, 74%, 74%, 75%, 75%, 76%, 77%, 78%, 79%, 80%, 81%, 82%, 83%, 84%, 85%, or more.

In certain embodiments, the AUC value is about 60% to about 86%; about 65% to about 86%; about 70% to about 86%; about 75% to about 86%; about 80% to about 86%; about 82% to about 86%; about 84% to about 86%; or about 84% to about 85%.

In certain embodiments, the AUC value is up to about 61%, 62%, 63%, 64%, 65%, 66%, 67%, 68%, 69%, 70%, 71%, 72%, 73%, 73%, 74%, 74%, 75%, 75%, 76%, 77%, 78%, 79%, 80%, 81%, 82%, 83%, 84%, or 85%.

In certain embodiments of the methods provided herein, the sensitivity of the method is about 70% to about 80%; about 70% to about 75%; or about 75% to about 80%.

In certain embodiments of the methods provided herein, the specificity of the method is about 70% to about 81%; about 73% to about 81%; or about 70% to about 73%.

In certain embodiments of the methods provided herein the sensitivity of the method is about 70% to about 80% and the corresponding specificity is about 81% to about 70%; the sensitivity of the method is about 70% to about 75% and the corresponding specificity is about 81% to about 73%; or the sensitivity of the method is about 75% to about 80% and the corresponding specificity is 73% to about 70%.

In instances where concentration of one or more urinary polyamines in the sample indicates the individual is susceptible to prostate cancer, one or more confirmatory prostate cancer tests can be used to confirm whether the individual suffers from prostate cancer. Accordingly, the methods described can further comprise the step of conducting one or more prostate cancer examinations on the individual to determine (e.g., to confirm) if the individual has prostate cancer.

The prostate cancer examination can be any prostate cancer test used to diagnosis prostate cancer, such as a digital rectal examination, the prostate specific antigen test, prostate biopsy, TRUSPB, magnetic resonance imaging (MRI) scan of the prostate, and combinations thereof.

If the one or more confirmatory prostate cancer tests confirms that the individual suffers from prostate cancer, the individual can be treated for prostate cancer. Accordingly, the methods provided herein can further comprise the step of treating the individual for prostate cancer.

Multiple treatment options exist for prostate cancer and new ones are being developed. In current practice, the three most common treatment options for men with screen-detected, localized prostate cancer are surgical removal of the prostate gland (radical prostatectomy), radiation therapy (external-beam radiation therapy, proton beam therapy, or brachytherapy), and the like.

Accordingly, the method of treating the prostate cancer can include surgery, radiation, cryosurgery, thermotherapy, hormone treatment, chemotherapy, vaccines, photodynamic therapy, and other immunotherapies, or combinations thereof.

The method of treating the prostate cancer can also include prophylaxis to prevent or delay development or progression of the prostate cancer.

Prostate cancer treatment also includes surveillance of the severity and/or progression of the prostate cancer in the individual. If the severity worsens and/or surrounding circumstances dictate, the individual can then be treated for prostate cancer.

Part 2: Synthesis of Lanthanide Complexes for Spm Sensing

A series of lanthanide compounds (1) was developed that are useful in the colorimetric quantitative and qualitative analysis of urinary polyamines.

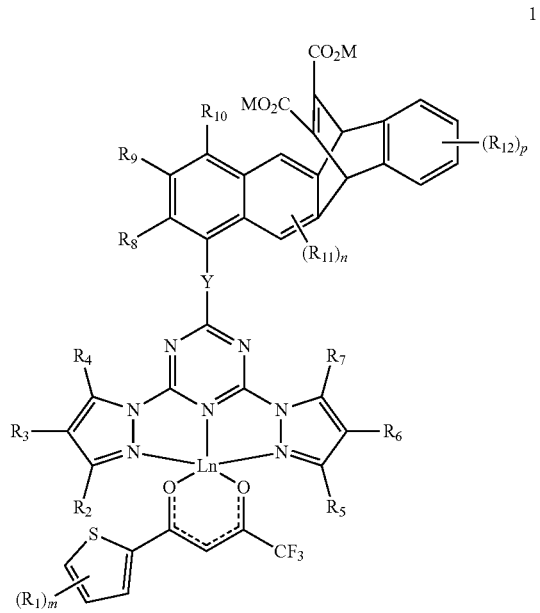

wherein m is 1, 2, or 3;
n for each occurrence is independently 1 or 2;
p for each occurrence is independently is 1, 2, 3, or 4;
Ln is a lanthanide;
each M is independently selected from the group consisting of Na, Li, and K; or two M taken together represent Mg or Ca;
Y is —C≡C— or is absent;
$R_1$ for each instance is independently hydrogen, alkyl, or cycloalkyl;
each of $R_2$, $R_3$, $R_4$, $R_5$, $R_6$, and $R_7$ are independently selected from hydrogen, alkyl, cycloalkyl and aryl;
each of $R_8$ and $R_9$ are independently selected from hydrogen, halide, cyano, nitro, hydroxyl, ether, thioether, amine, amide, acylamino, ester, alkyl, cycloalkyl, heterocycloalkyl, aryl, heteroaryl, alkene, and alkyne; or $R_8$ and $R_9$ taken together form a moiety selected from the group consisting of:

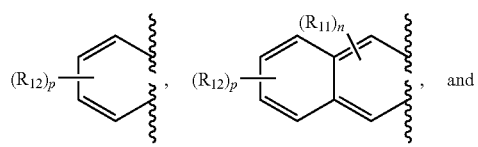 and

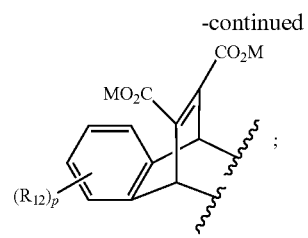

$R_{10}$ is hydrogen, halide, cyano, nitro, hydroxyl, ether, thioether, amine, amide, acylamino, ester, alkyl, cycloalkyl, heterocycloalkyl, aryl, heteroaryl, alkene, or alkyne; or $R_{10}$ is a moiety having the structure:

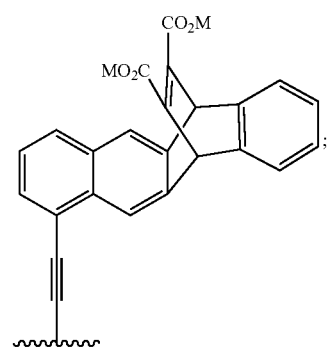

and each instance of $R_{11}$ and $R_{12}$ is independently selected from hydrogen, halide, cyano, nitro, hydroxyl, ether, thioether, amine, amide, acylamino, ester, alkyl, cycloalkyl, heterocycloalkyl, aryl, heteroaryl, alkene, and alkyne. In certain embodiments, the compound of Formula 1 described herein do not include a compound of Formula 2:

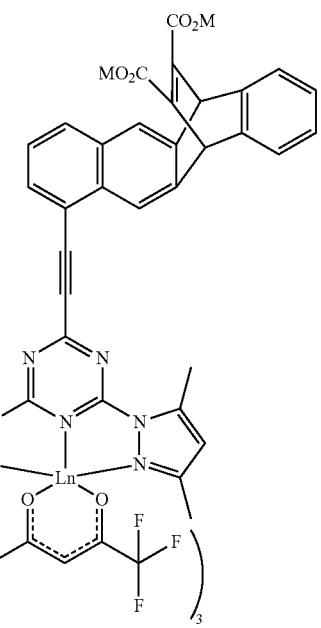
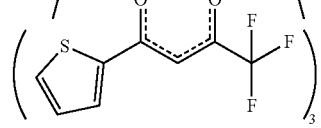

wherein Ln is a lanthanide; and each M is independently selected from the group consisting of Na, Li, and K; or two M taken together represent Mg or Ca.

In certain embodiments, Ln is a lanthanide selected from the group consisting of La, Ce, Pr, Nd, Pr, Nd, Pm, Eu, Gd, Tb, Dy, Ho, Er, Tm, Yb, and Lu. The lanthanide can be in any oxidation state. Exemplary, oxidation states include, but are not limited to +2, +3, and +4. In certain embodiments, the lanthanide is in the +3 oxidation state. In certain embodiments, the lanthanide is $Eu^{3+}$.

In certain embodiments, $R_2$, $R_3$, $R_4$, $R_5$, $R_6$, and $R_7$ are independently selected from hydrogen and alkyl. In certain embodiments, $R_2$, $R_4$, $R_5$, and $R_7$ are independently alkyl; and $R_3$ and $R_6$ are hydrogen.

In certain embodiments, each of $R_8$ and $R_9$ are independently selected from hydrogen, halide, cyano, nitro, hydroxyl, ether, thioether, amine, amide, acylamino, ester, alkyl, cycloalkyl, heterocycloalkyl, aryl, and heteroaryl; or $R_8$ and $R_9$ taken together form a moiety selected from the group consisting of:

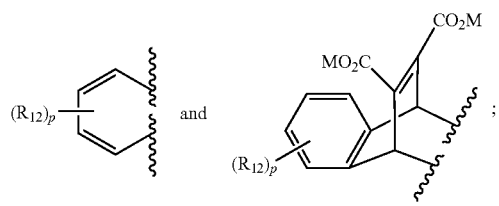

wherein $R_{12}$ is independently selected from hydrogen, halide, cyano, nitro, hydroxyl, ether, thioether, amine, amide, acylamino, ester, alkyl, cycloalkyl, heterocycloalkyl, aryl, and heteroaryl.

In certain embodiments, each of $R_8$ and $R_9$ are independently selected from hydrogen, halide, cyano, nitro, hydroxyl, ether, thioether, amine, amide, acylamino, ester, alkyl, cycloalkyl, heterocycloalkyl, aryl, and heteroaryl; or $R_8$ and $R_9$ taken together form a moiety selected from the group consisting of:

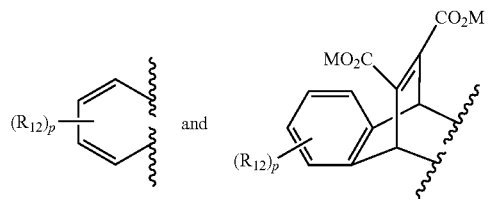

wherein $R_{12}$ is independently selected from hydrogen, halide, cyano, nitro, hydroxyl, ether, thioether, amine, amide, acylamino, ester, alkyl, cycloalkyl, heterocycloalkyl, aryl, and heteroaryl; and $R_{10}$ is amine or represented by the following moiety:

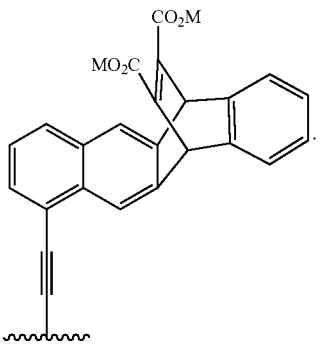

In certain embodiments, provide herein is a compound represented by the Formula 3:

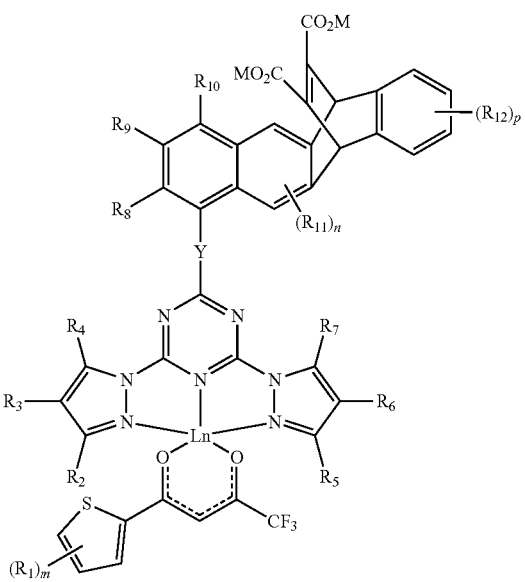

3 wherein m is 1, 2, or 3;

n for each occurrence is independently 1 or 2;

p for each occurrence is independently is 1, 2, 3, or 4;

Ln is a lanthanide;

each M is independently selected from the group consisting of Na, Li, and K; or two M taken together represent Mg or Ca;

Y is —C≡C— or is absent;

$R_1$ for each instance is independently hydrogen, alkyl, or cycloalkyl;

each of $R_2$, $R_3$, $R_4$, $R_5$, $R_6$, and $R_7$ are independently selected from hydrogen, alkyl, cycloalkyl and aryl;

each of $R_8$ and $R_9$ are independently selected from hydrogen, halide, cyano, nitro, hydroxyl, ether, thioether, amine, amide, acylamino, ester, alkyl, cycloalkyl, heterocycloalkyl, aryl, heteroaryl, alkene, and alkyne;

$R_{10}$ is hydrogen, halide, cyano, nitro, hydroxyl, ether, thioether, amine, amide, acylamino, ester, alkyl, cycloalkyl, heterocycloalkyl, aryl, heteroaryl, alkene, or alkyne; and each instance of $R_{11}$ and $R_{12}$ is independently selected from hydrogen, halide, cyano, nitro, hydroxyl, ether, thioether, amine, amide, acylamino, ester, alkyl, cycloalkyl, heterocycloalkyl, aryl, heteroaryl, alkene, and alkyne.

In certain embodiments, the compound of Formula 3 described herein do not include a compound of Formula 2:

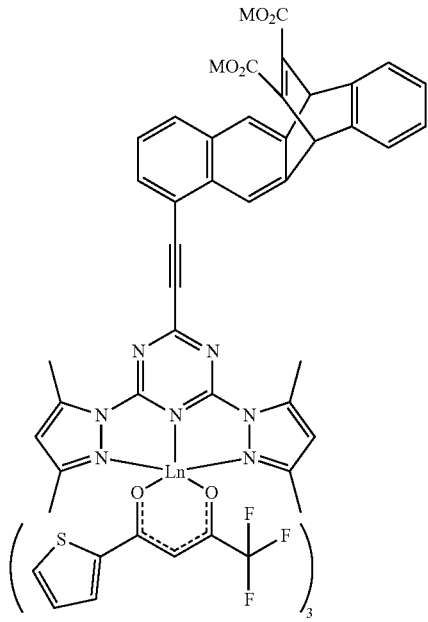

wherein Ln is a lanthanide; and each M is independently selected from the group consisting of Na, Li, and K; or two M taken together represent Mg or Ca.

In certain embodiments of the compound of Formula 3, Y is —C≡C—; each instance of $R_1$ is independently hydrogen or alkyl; $R_2$, $R_4$, $R_5$, and $R_7$ are independently alkyl; $R_3$ and $R_6$ are hydrogen; $R_8$ and $R_9$ are independently selected from hydrogen, halide, cyano, nitro, ether, thioether, amine, amide, acylamino, ester, alkyl, cycloalkyl, heterocycloalkyl, aryl, and heteroaryl; and $R_{10}$ is hydrogen, halide, cyano, nitro, hydroxyl, ether, thioether, amine, amide, acylamino, ester, alkyl, cycloalkyl, heterocycloalkyl, aryl, or heteroaryl.

In certain embodiments of the compound of Formula 3, $R_1$ is hydrogen; each of $R_2$, $R_3$, $R_4$, $R_5$, $R_6$, and $R_7$ are independently selected from hydrogen and alkyl; each of $R_8$ and $R_9$ are independently selected from hydrogen, halide, cyano, nitro, hydroxyl, ether, thioether, amine, amide, acylamino, ester, alkyl, cycloalkyl, heterocycloalkyl, aryl, and heteroaryl; $R_{10}$ is hydrogen, halide, cyano, nitro, hydroxyl, ether, thioether, amine, amide, acylamino, ester, alkyl, cycloalkyl, heterocycloalkyl, aryl, or heteroaryl; and each instance of $R_{11}$ and $R_{12}$ is independently selected from hydrogen, halide, cyano, nitro, hydroxyl, ether, thioether, amine, amide, acylamino, ester, alkyl, cycloalkyl, heterocycloalkyl, aryl, and heteroaryl.

In certain embodiments of the compound of Formula 3, $R_1$ is hydrogen; each of $R_2$, $R_4$, $R_5$, and $R_7$ are independently selected from hydrogen and alkyl; $R_3$ and $R_6$ are hydrogen; each of $R_8$ and $R_9$ are independently selected from hydrogen, halide, cyano, nitro, hydroxyl, ether, thioether, amine, amide, acylamino, ester, alkyl, cycloalkyl, heterocycloalkyl, aryl, and heteroaryl; $R_{10}$ is hydrogen, halide, cyano, nitro, hydroxyl, ether, thioether, amine, amide, acylamino, ester, alkyl, cycloalkyl, heterocycloalkyl, aryl, or heteroaryl; and each instance of $R_{11}$ and $R_{12}$ is independently selected from hydrogen, halide, cyano, nitro, hydroxyl, ether, thioether, amine, amide, acylamino, ester, alkyl, cycloalkyl, heterocycloalkyl, aryl, and heteroaryl.

In certain embodiments, the compound of Formula 3 is the following compound:

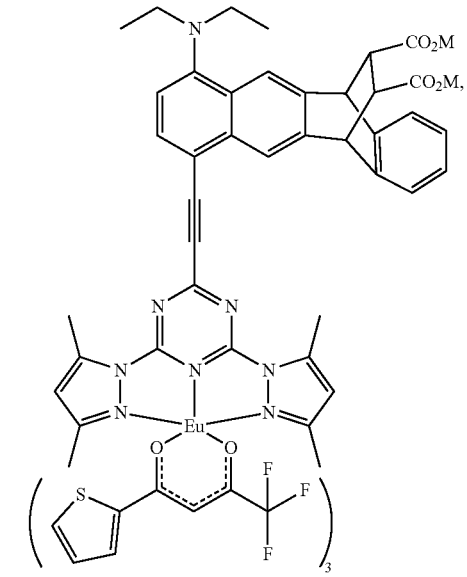

wherein M is lithium or sodium.

In certain embodiments, provide herein is a compound represented by the Formula 4:

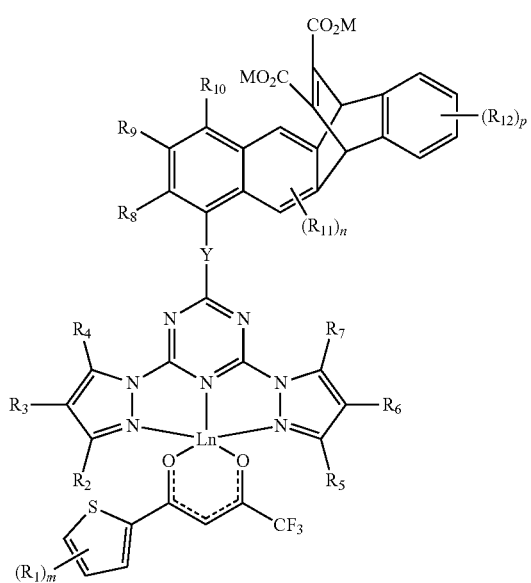

wherein m is 1, 2, or 3;

n for each occurrence is independently 1 or 2;

p for each occurrence is independently is 1, 2, 3, or 4;

Ln is a lanthanide;

each M is independently selected from the group consisting of Na, Li, and K; or two M taken together represent Mg or Ca;

Y is —C≡C— or is absent;

R₁ for each instance is independently hydrogen, alkyl, or cycloalkyl;

each of $R_2$, $R_3$, $R_4$, $R_5$, $R_6$, and $R_7$ are independently selected from hydrogen, alkyl, cycloalkyl and aryl;

$R_8$ and $R_9$ taken together form a moiety selected from the group consisting of:

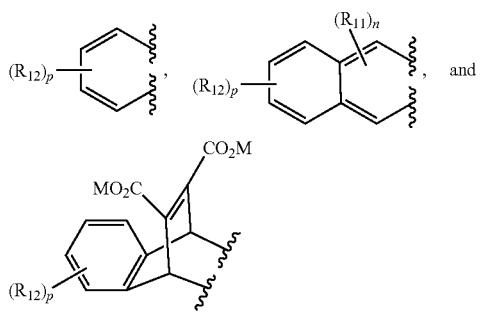

$R_{10}$ is hydrogen, halide, cyano, nitro, hydroxyl, ether, thioether, amine, amide, acylamino, ester, alkyl, cycloalkyl, heterocycloalkyl, aryl, heteroaryl, alkene, or alkyne; or $R_{10}$ is a moiety having the structure:

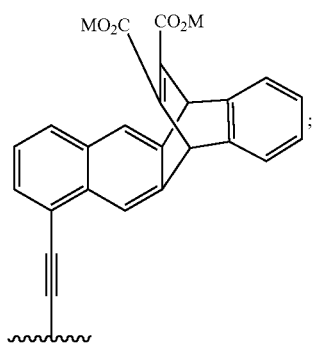

or each of $R_8$ and $R_9$ are independently selected from hydrogen, halide, cyano, nitro, hydroxyl, ether, thioether, amine, amide, acylamino, ester, alkyl, cycloalkyl, heterocycloalkyl, aryl, heteroaryl, alkene, and alkyne and $R_{10}$ is a moiety having the structure:

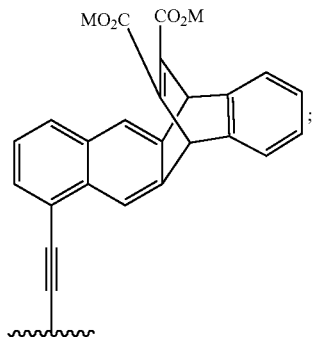

and each instance of $R_{11}$ and $R_{12}$ is independently selected from hydrogen, halide, cyano, nitro, hydroxyl, ether, thioether, amine, amide, acylamino, ester, alkyl, cycloalkyl, heterocycloalkyl, aryl, heteroaryl, alkene, and alkyne.

In certain embodiments of the compound of Formula 4, $R_1$ is hydrogen; each of $R_2$, $R_3$, $R_4$, $R_5$, $R_6$, and $R_7$ are independently selected from hydrogen and alkyl; and each instance of $R_{11}$ and $R_{12}$ is independently selected from hydrogen, halide, cyano, nitro, hydroxyl, ether, thioether, amine, amide, acylamino, ester, alkyl, cycloalkyl, heterocycloalkyl, aryl, heteroaryl, and alkene.

In certain embodiments, the compound of Formula 4 is selected from the group consisting of:

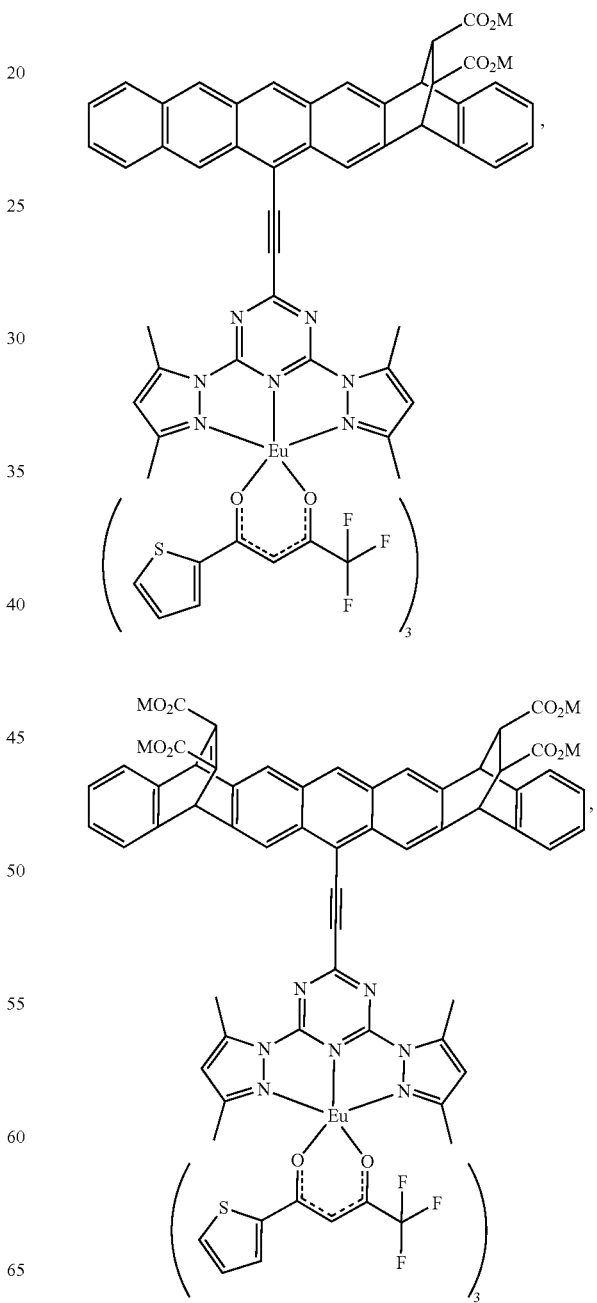

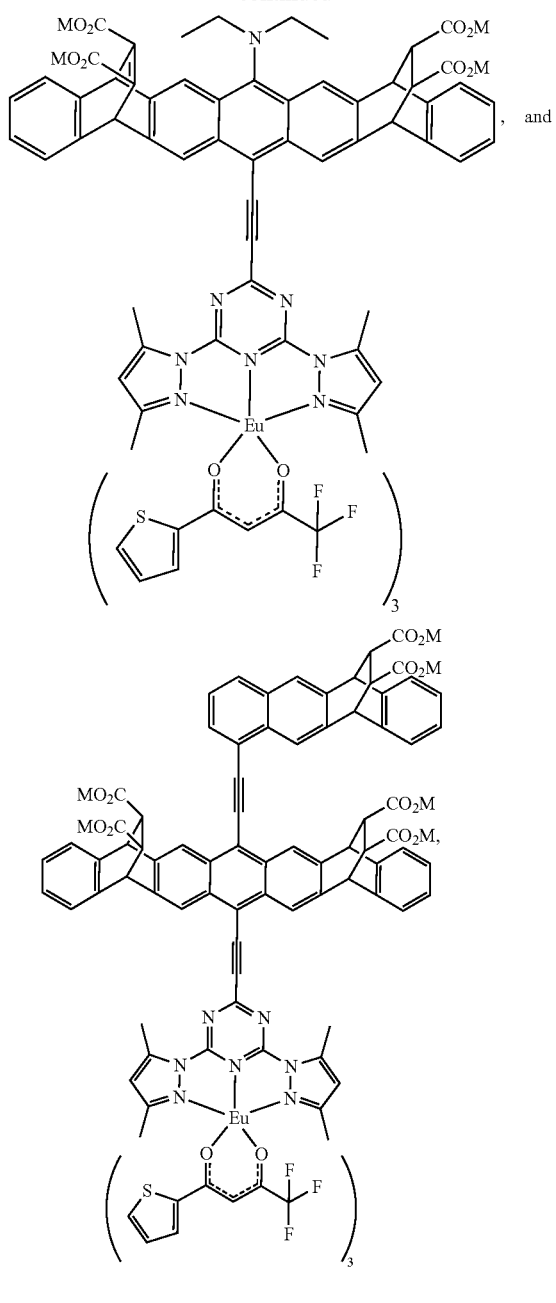
, and
wherein M is lithium or sodium.
Compounds of Formula 1 can be synthesized using any number of conventional methods. An exemplary synthetic sequence employing a [4+2] Diels-Alder reaction is depicted in the scheme below.
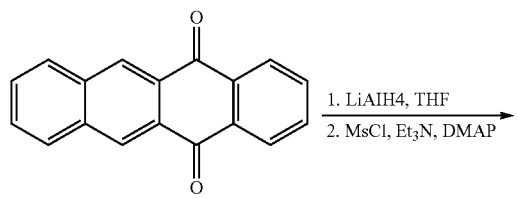
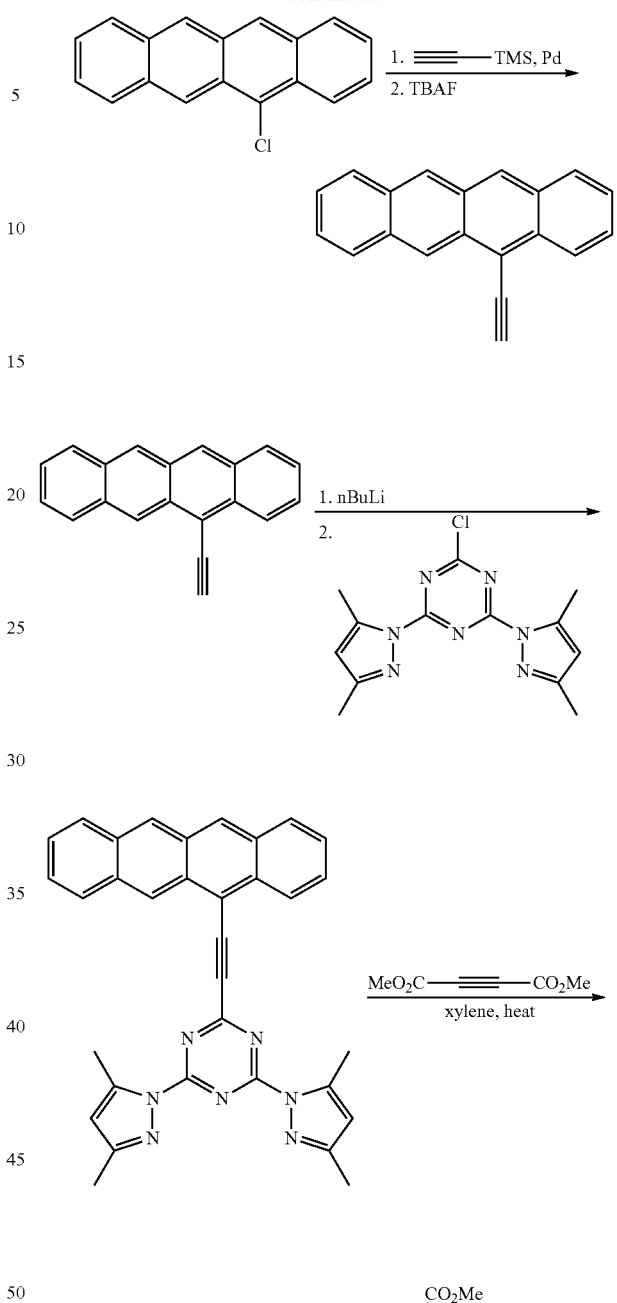

-continued

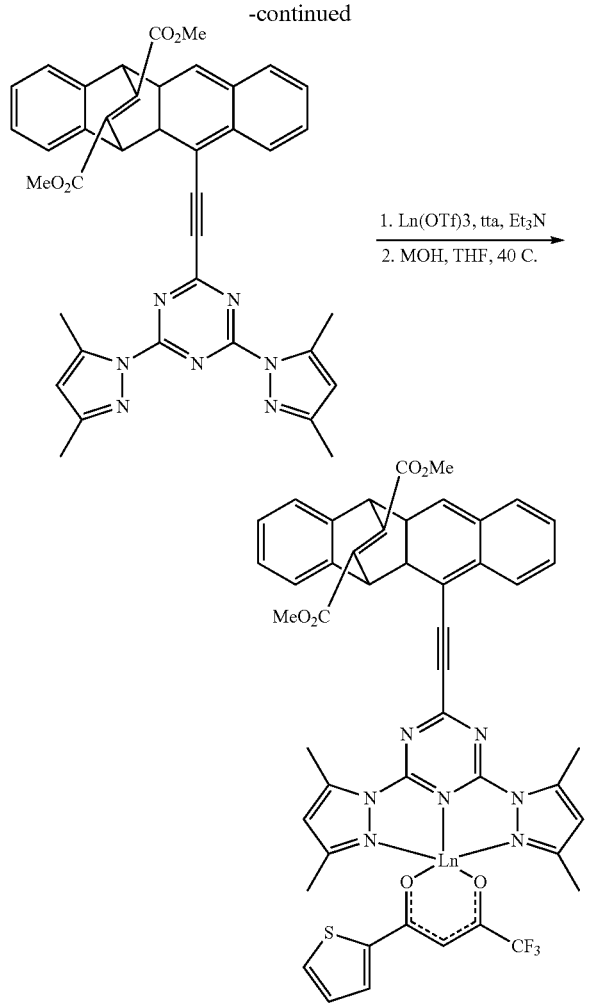

By the appropriate modification of the starting materials optionally in combination with further synthetic transformations, other compounds of Formula 1 can be prepared. The selection of the appropriate starting materials and the necessary further synthetic transformations needed to prepare other compounds of Formula 1 is well within the skill of a person of ordinary skill in the art.

Figure 7A:
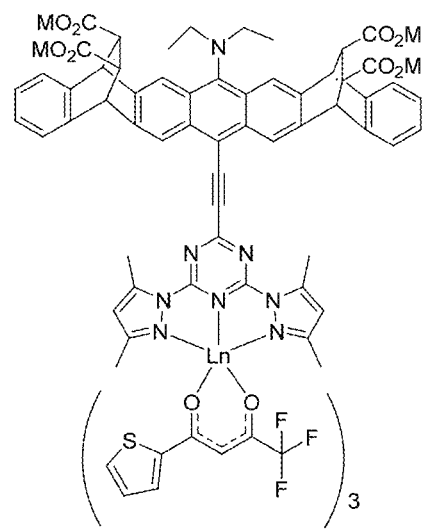
FIG. 7A shows the chemical structure of an exemplary lanthanide complex 1.
Figure 7B:
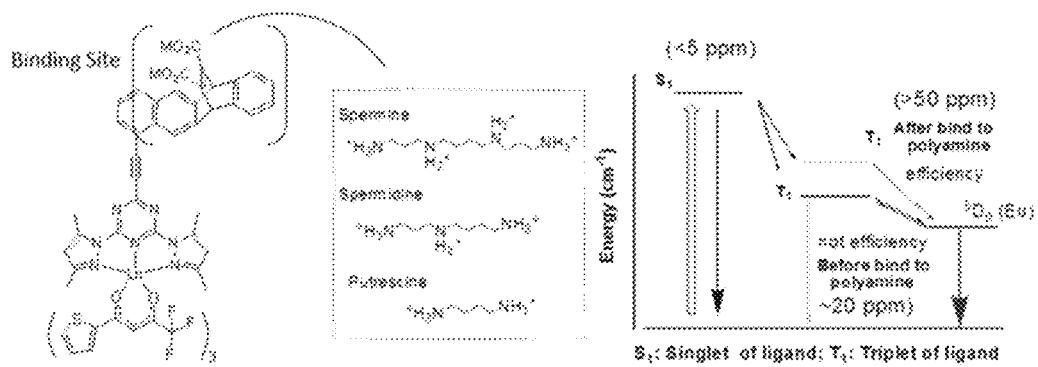
FIG. 7B shows the schematic representations of colour changing lanthanide-based polyamines chemosensors where the design is based on polyamine-activated f-f emission.
Figure 7B:
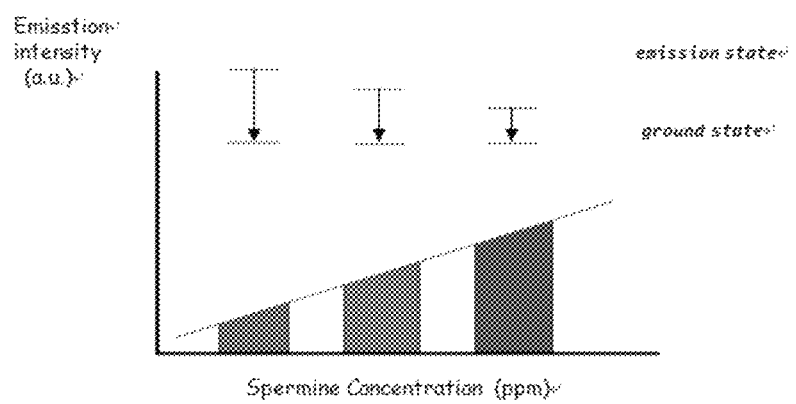
Figure 7B:
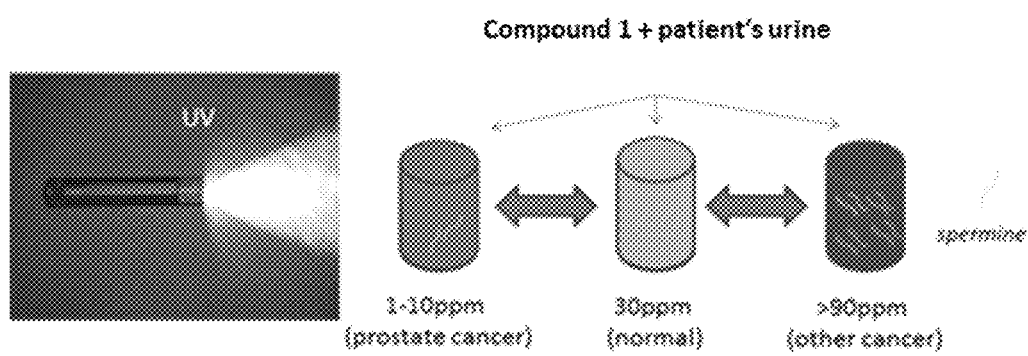

Without wishing to be bound by theory, it is believed that Put and n-butylamine are significantly less effective than Spm and Spd in binding multiple poly(p-phenylene ethylene (PPE) chains (i.e., the upper portion of the compound of Formula 1) to form tightly associated aggregates with enhanced inter-chain exciton migration. Therefore, a chemical sensor based on nonspecific electrostatic interactions could still exhibit some selectivity between similar analytes, with high means, it binds better to Spm (+4 charged) and Spd (+3 charged) and worse to putrescine (+2 charged) and n-butylamine (+1 charged) (FIGS. 7A-7B).

Figure 14:
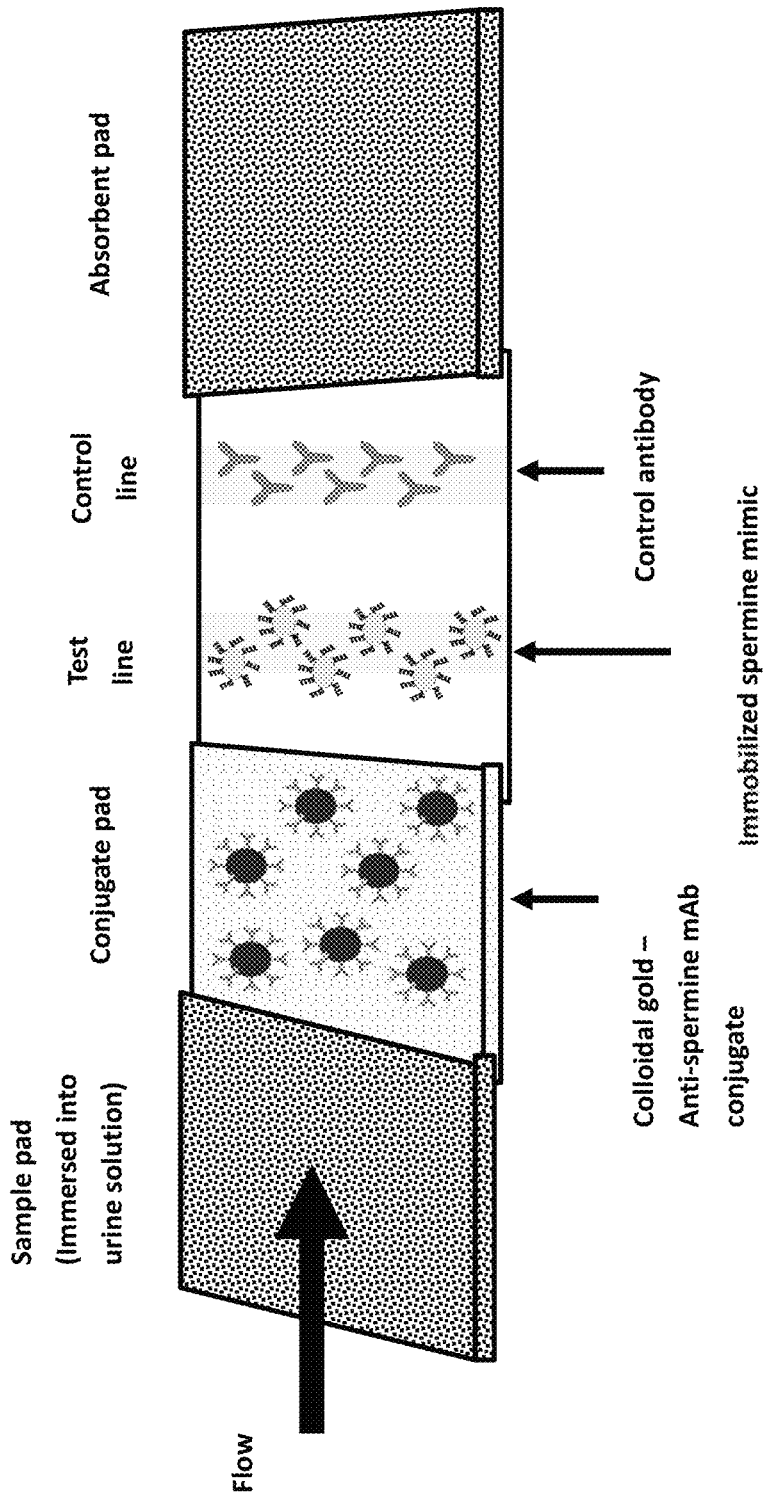
FIG. 14 shows the schematic illustration of an exemplary PCa-biomarker sensing strip comprising compound described herein.
Figure 15A:
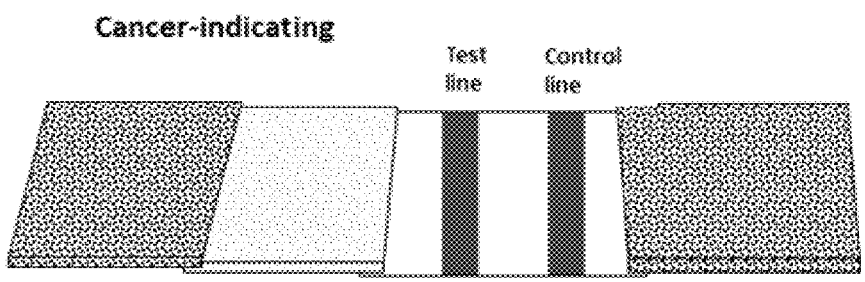
FIG. 15A shows the interpretations of an exemplary PCa diagnostic strip with cancer indicating.
Figure 15B:
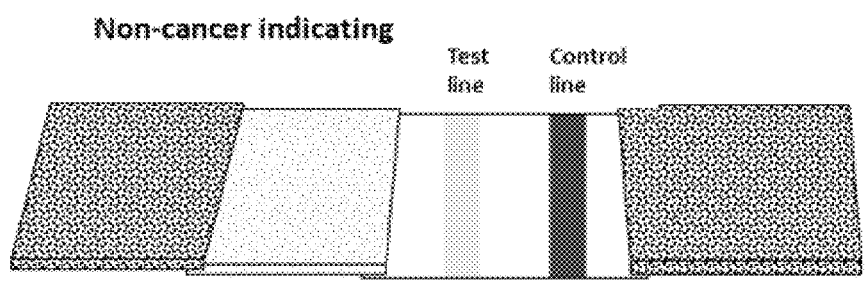
FIG. 15B shows the interpretations of an exemplary PCa diagnostic strip with non-cancer-indicating.
Figure 15C:
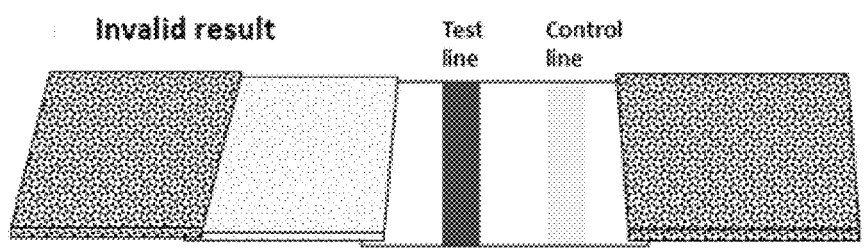
FIG. 15C shows the interpretations of an exemplary PCa diagnostic strip with invalid result.
Figure 15D:
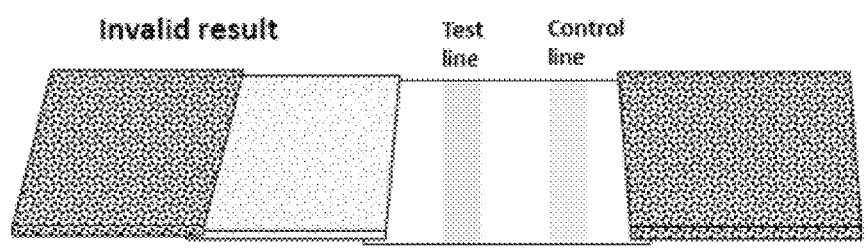
FIG. 15D shows the interpretations of an exemplary PCa diagnostic strip with invalid result.
Figure 15E:
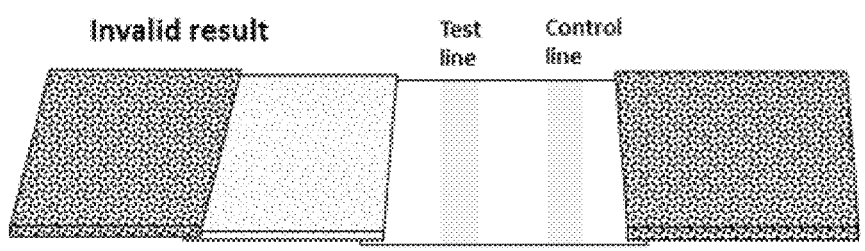
FIG. 15E shows the interpretations of an exemplary PCa diagnostic strip with invalid result.

Also provided is a test device comprising the compound of Formula 1 useful for determining the levels of one or more urinary polyamines in a sample. The test device can be a test strip or a dipstick. FIGS. 14-15E depict test strips useful for determining the level of one or more urinary polyamines in a sample. The test strip comprises the compound of Formula 1.

The test strips in FIGS. 14-15E can also be used in connection with enzymatic methods for detecting urinary polyamines.

In certain embodiments, provided herein are kits useful for determining the level of one or more urinary polyamines in a sample comprising a compound of Formula 1 and instructions for conducting the methods described herein.

In certain embodiments, the kit useful for determining the level of one or more urinary polyamines in a sample comprises a testing device, such as a dipstick or a test strip comprising the compound of Formula 1 and instructions for conducting the methods described herein using the test strip.

In certain embodiments, the kits further comprise a calibrated reference color chart, which provides a correlation between the color of the test sample and the concentration of the one or more urinary polyamines in the test sample.

In certain embodiments, the kits further comprise at least one of an ROC chart and/or table and an AUC chart/table for spermine that correlates the concentration of spermine in the test sample with the likelihood that the individual suffers from prostate cancer.

Figure 8A:
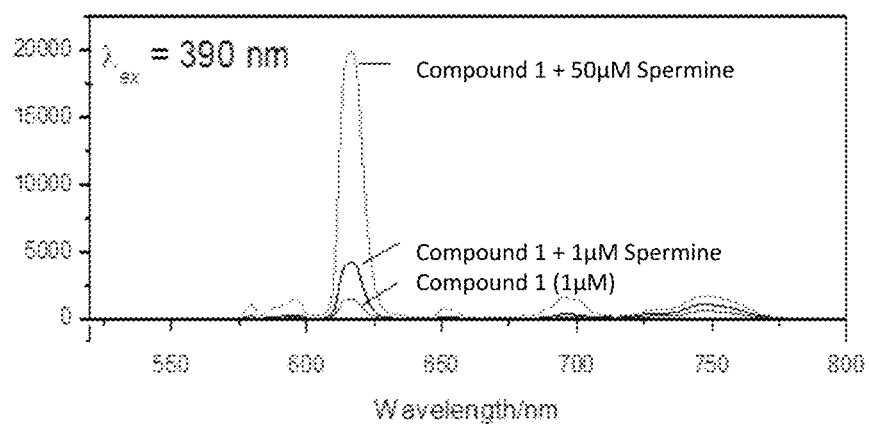
FIG. 8A shows Eu emission enhancement after compound 2 (1 µM) binds with Spm (1 µM).
Figure 8B:
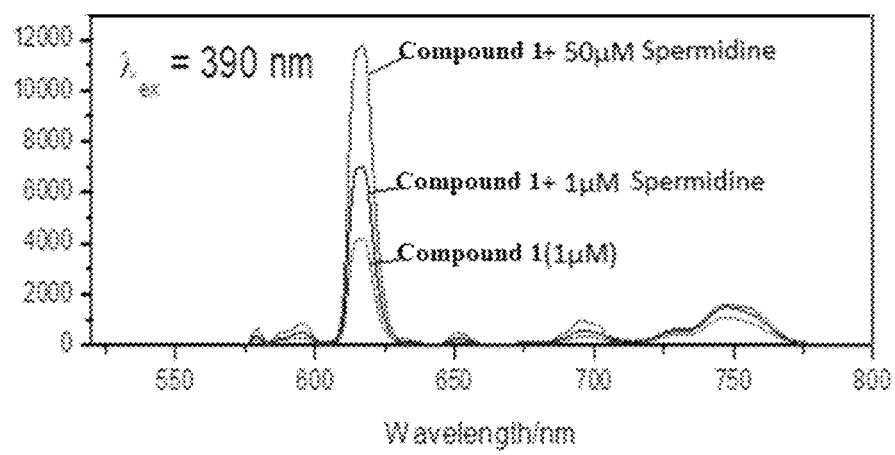
FIG. 8B shows Eu emission enhancement after compound 2 (1 µM) binds with Spd (50 µM).
Figure 8C:
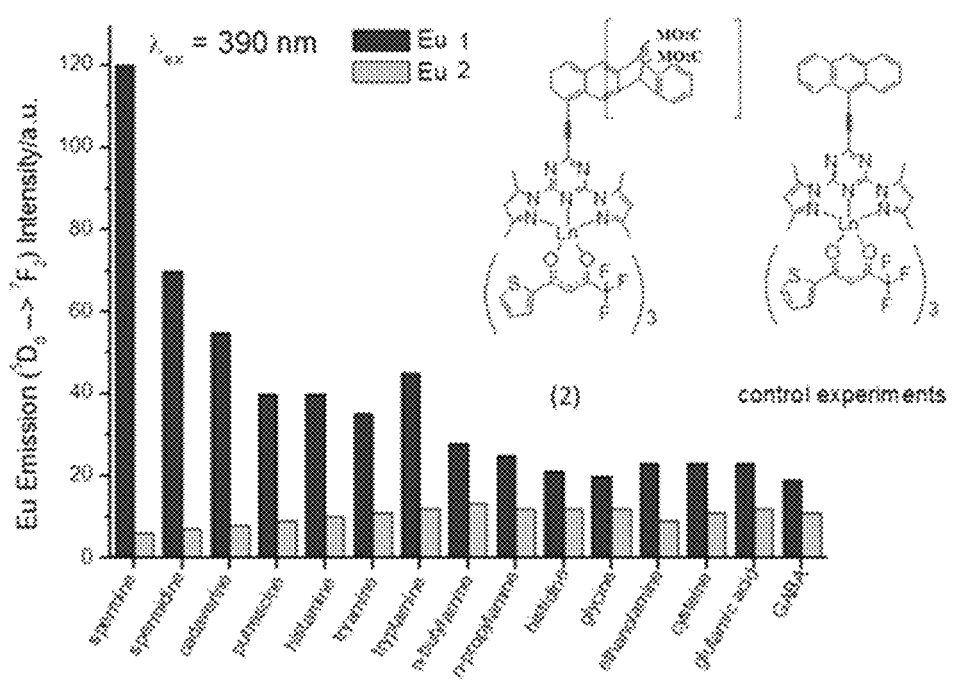
FIG. 8C shows the selectivity of compound 2 for Spm and Spd over various biogenic amines and cations in aqueous DMSO (3%-DMSO).

Ligation of the Newly Developed Chromophore to Lanthanide Complexes Reveals Strong Binding and Specific Selectivity for Polyamines Through Linear/Two-Photon Excitation Compound 1 was synthesized with the polyamines-specific binding site. The conjugated system controlled the triplet state of triazine-based ligand and gives green emission of the ligand. The two anionic groups in compound 1 (FIG. 7B) served as the binding to the positive charge polyamine, which is thermodynamically favourable. The multicationic analyte can interrupt the conjugated system in the complex. Four structural red f-f ($^5D_0 \rightarrow ^7F_J$, J=1-6) emission bands can be obtained from compound 1 upon excitation at 390 nm (FIGS. 8A-8C). The quantum yield (Φ) and lifetime of compound 2 are 0.05 and 0.83 ms respectively in the solution of DMSO:$H_2O$. After the complexes bind with the Spm and Spd (50 M), the emission intensity and quantum yield increase by more than 30% (the concentration of Spm and Spd in tumor blood samples are ~10 M and 46 M respectively).

Titration of Europium Compound (2) with Spm and Spd

The significant f-f emission enhancement can be visualized under UV-excitation after compound 1 binds with polyamines (FIGS. 8A and 8B). The control experiments had been done with the control europium compound (FIG. 7A); no significant emission changes can be observed with the addition of polyamines. (Inset of FIG. 8C motif structure of control compound without anionic binding sites for polyamine) Binding ratio (1:1) and constant (3×10$^{-5}$M) between compound 1 and polyamines had been determined by the $^5D_0 \rightarrow ^7F_2$ emission intensity with various concentration of Spm. The lifetime variations of the binding of polyamines had been monitored rather than emission. (Responsive milli-second lifetime changes have great potential for the new generation of in-situ polyamine sensors with the help of time gated system; it can eliminate the nano-/micro-second interference in the fluid/blood samples).

Selectivity of Lanthanide Complexes for Spm and Spd

The selectivity of compound 2 for Spm and Spd over other bioactive cations, such as $K^+$, $Na^+$, $Ca^{2+}$, and other biogenic amines is presented in FIG. 8B. This is particularly important because these biogenic amines can interfere with the response of polyamines to the proposed complexes in-situ. No significant interference is observed by other biogenic amines and cations. The selectivity of compound 2 for Spm and Spd is significantly greater than that for other common bioactive cations and biogenic amines (FIG. 8B). Control experiments were also conducted with a control europium complex, which did not exhibit any significant $^5D_0 \rightarrow {}^7F_2$ emission enhancement in the presence of all of the tested biogenic amines and cations.

Preliminary Clinical Trial with 10 Prostate Cancer Patients' Urine Samples

Figure 9A:
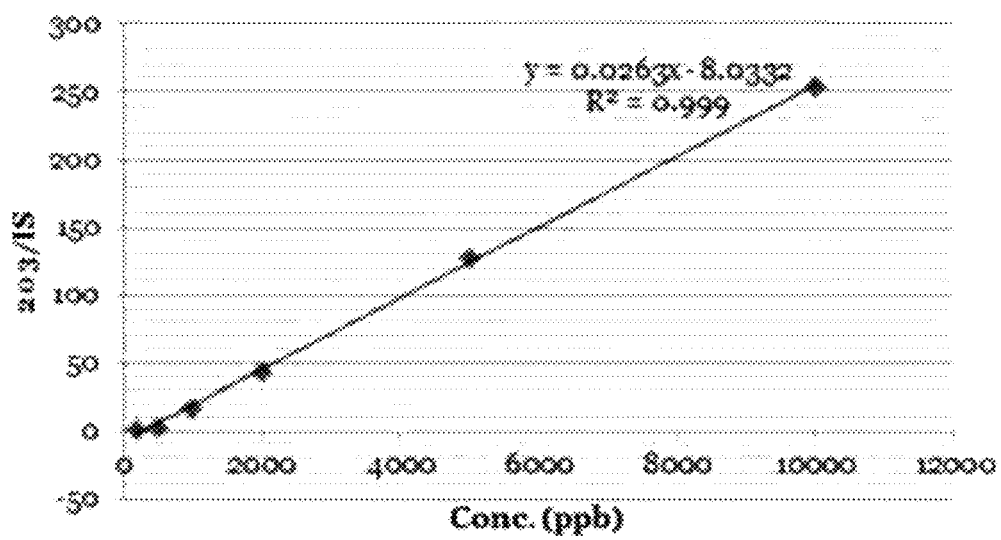
FIG. 9A shows the calibration of Spm level in 10 prostate cancer patients' urine samples.

More than 150 urine samples from prostate cancer patients were collected and analyzed for their Spm level by the standard protocol. (Creatinine level done by Jaffe's method and polyamine level checked with LC-MS/MS). The calibration curve of numerous polyamines (FIG. 9A), such as Spm—FIG. 9B and Spd have been worked out and the concentrations of these polyamine levels had been sorted out. The level determined was similar to the findings from Dr. Häkkinen in 2014.

Figure 10:
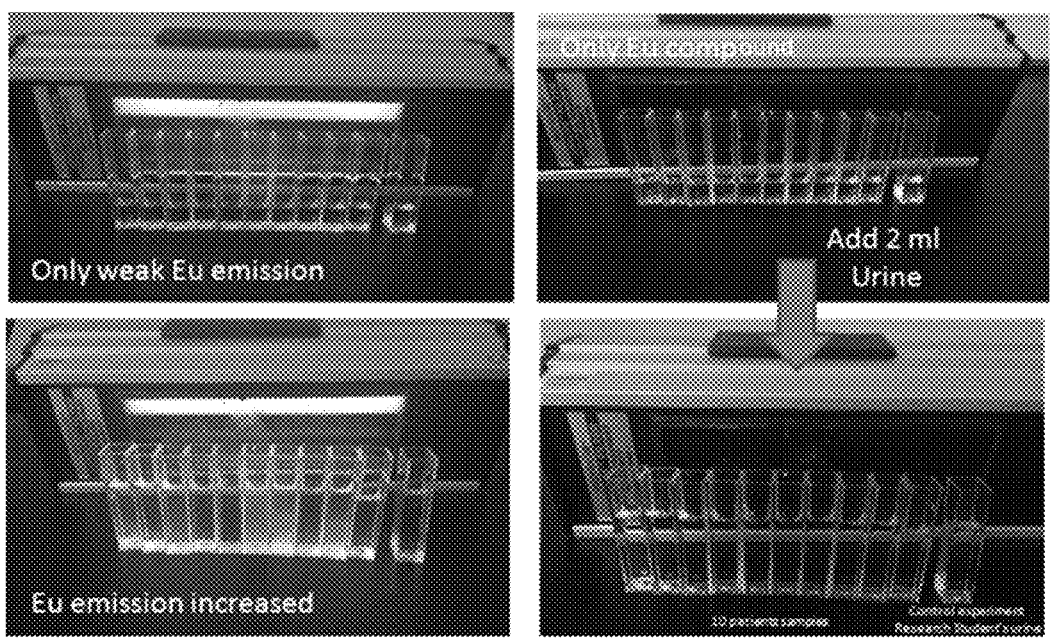
FIG. 10 shows the photographs of europium compound 2 (10 µM in aqueous solution) showing the color change in the presence of 10 prostate cancer patients urine samples under UV excitation. One urine sample from the research student was examined as the control experiment.

A series of prostate cancer patient's urine samples were selected for pre-clinical trial. Their polyamine contents were pre-determined by LC and shown in FIGS. 9A-9B. In FIG. 10, the photograph of compound 1 (10 mM in aqueous solution) shows the color change only in the presence of 10 prostate cancer patient's urine samples under the UV light. The polyamine concentration of the urine samples are evaluated by LCMS and internal standard.

Experiment-wise, 2 mL of patient urine samples will be added into 1 mL europium sensor solution (final concentration of the Eu sensor will be 50 μM). The samples will be placed in the spectrofluorometer and the responsive emission and emission lifetime signal changes will be monitored. The inventor also will monitor the emission spectra of the proposed complexes with the urine from the healthy volunteers as the control.

Figure 11:
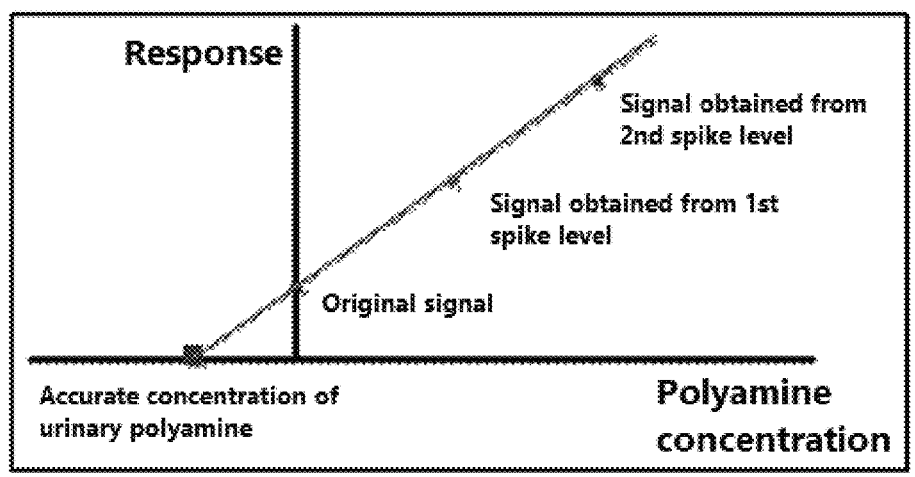
FIG. 11 shows the standard addition approach to define the concentrations of polyamines in urine samples.
Figure 12A:
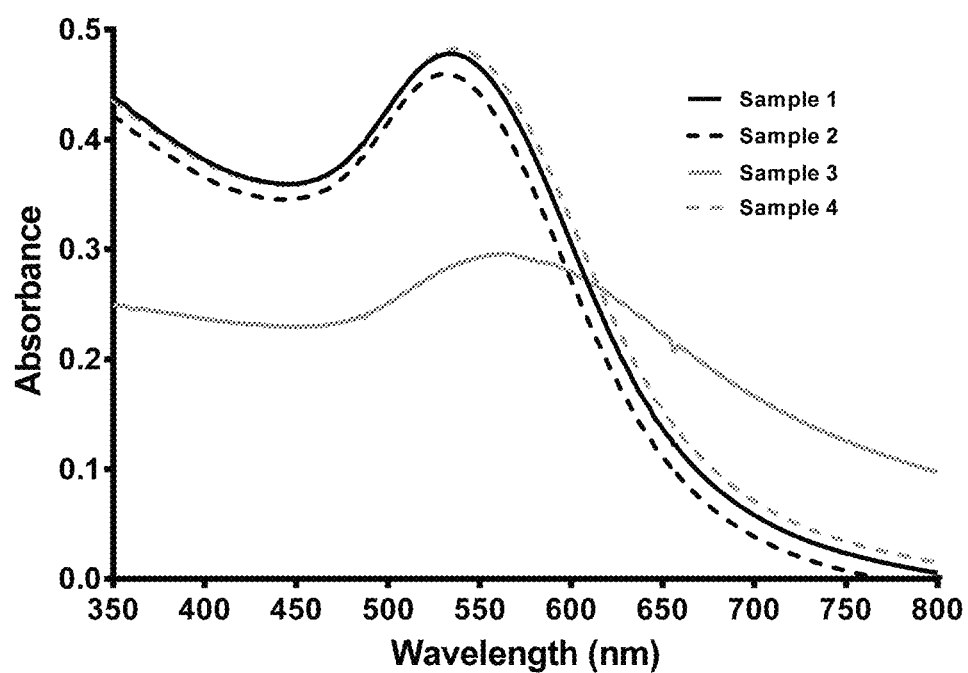
FIG. 12A shows Matrix effect of four urine samples before deproteinization.
Figure 12B:
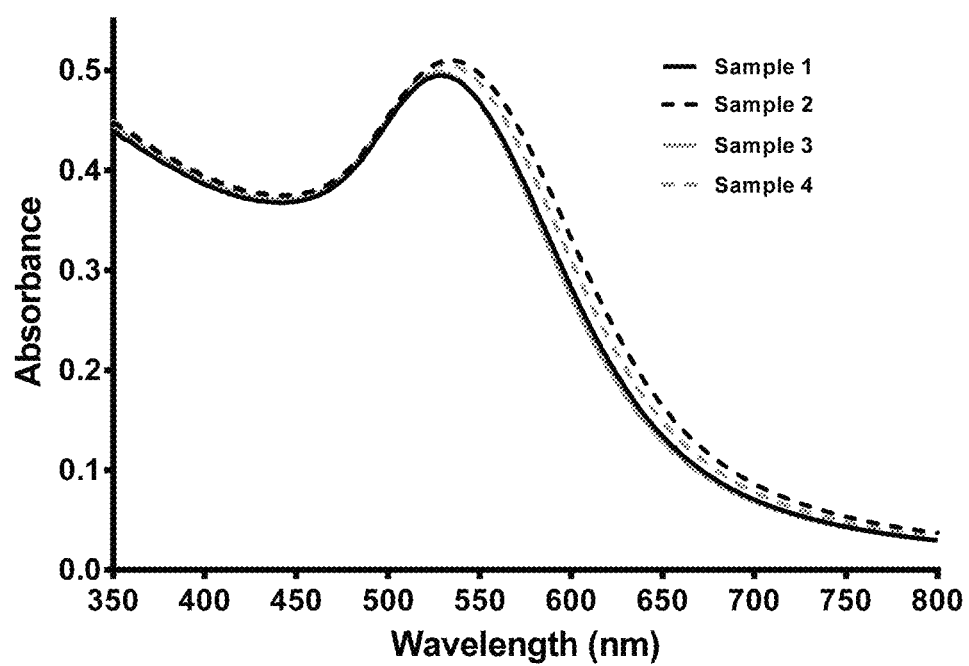
FIG. 12B shows Matrix effect of four urine samples after deproteinization.
Figure 12C:
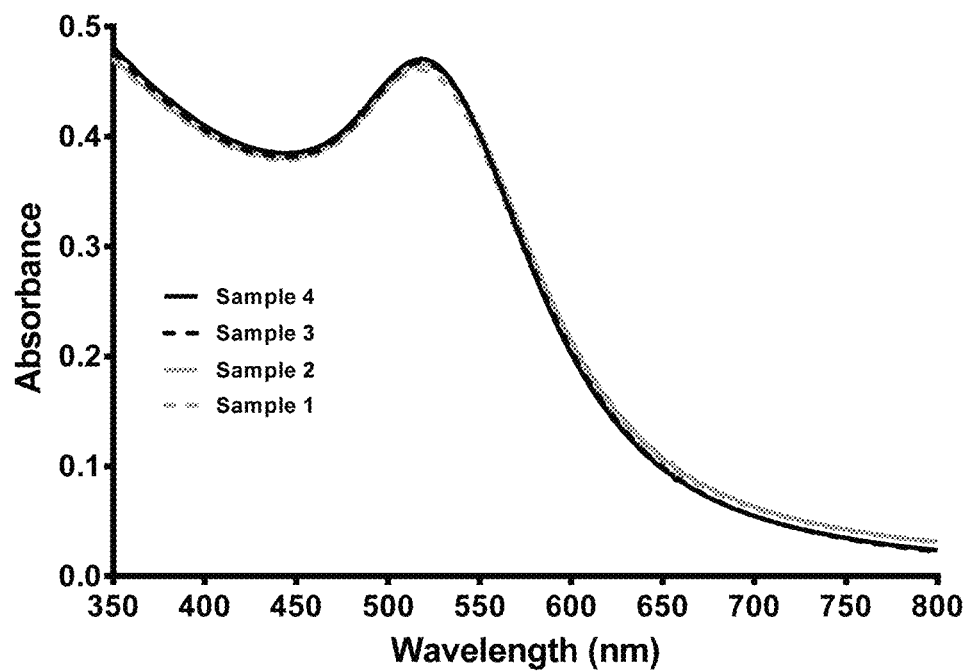
FIG. 12C shows Matrix effect of four urine samples after deproteinization and increasing DNA concentration to 100 nM.
Figure 13:
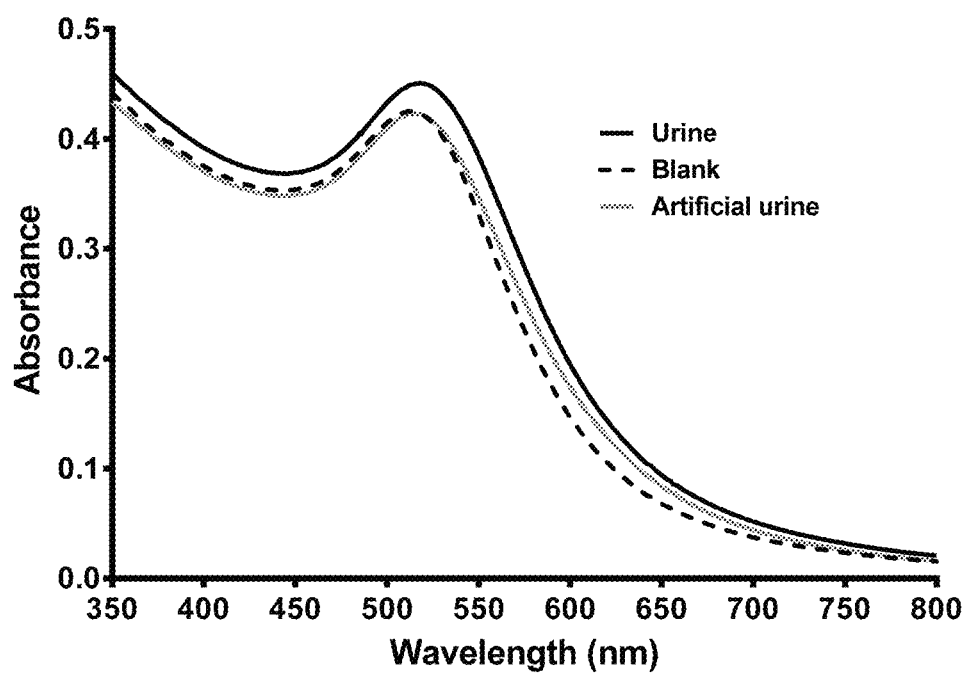
FIG. 13 shows the comparison of matrix effect of urine, blank ($H_2O$) and artificial urine.

Standard addition method, as shown in FIG. 11, will be used for the quantification by our developed bioprobe, which is a common method to solve the problems from matrix effect. Briefly, the signal of polyamines in urine sample will be measured and the result is plotted at concentration=x. The reading of 2 spiked levels will be measured, usually the 1 fold and 2 folds of the original concentration. The concentration of spiked level is written at x+A and x+B respectively. Upon extrapolating to the zero signal at the x-axis, the concentrations of polyamines in urine samples can be determined on the x-axis.

The mean values obtained by the two approaches were compared by Student's t tests where $P<0.05$ is considered to be statistically significant. There are not much differences between the readings obtained from luminescent complexes and the HPLC-MS/MS ($P<0.05$) and those readings are varied in a small range (% RSD<10). The inventor can conclude that the inventor's luminescent complexes are sensitive and reliable to detect polyamines in the urine samples. Analysis of the variation of sample frequency with Spm/Spd concentrations will be undertaken using standard statistical packages running in Origin. Equations are used to model a Gaussian distribution.

Materials and Instrument

All chemicals were acquired from Aldrich (Hong Kong, China) and Meryer (Shanghai, China). Britton-Robinson (BR) buffer was prepared by mixing equal molar ratio of phosphoric acid, boric acid and acetic acid, and the pH was then tuned using sodium hydroxide solution. Artificial urine was prepared according to a recipe elsewhere. All standard solutions were prepared in purified water sold under the trademark Milli-Q® water. For urine samples, they were collected from Princes of Wales Hospital, The Chinese University of Hong Kong.

Dynamic Light Scattering (DLS) and zeta-potential measurements were achieved by a Zetasizer Nano-ZS90 System (Malvern Instruments, Shanghai, China). The UV-Vis absorption spectra were recorded using a Cary 8453 UV-Vis Spectrometer (Agilent, Hong Kong, China). Isothermal Titration Calorimetry study was achieved using MicroCal PEAQ-ITC Automated System (Malvern Instruments, Shanghai, China).

For urine sample analysis, liquid chromatography separation was done by an Agilent 1290 Infinity Quaternary LC System while mass analysis was done by an Agilent 6460 Triple Quadrupole mass spectrometer equipped with an Agilent Jet Stream technology electrospray ionization source (Agilent, Hong Kong, China). All the incubations were performed on a KS 260 Basic Orbital Shaker (IKA, Hong Kong, China).

Sample Pretreatment Procedures

Briefly, a urine sample was thawed naturally and centrifuged for 5 minutes at 13,000 rpm and 25° C. Then it was passed through strong anion exchange solid phase extraction cartridge (Phenomenex, Strata, 100 mg/3 mL, USA) to retain unwanted organic acids, phenolic compounds and carbohydrates. Afterwards the solution was treated with concentrated perchloric acid for further deproteinization, which was then removed by neutralization using potassium hydroxide solution to form insoluble potassium perchlorate salt. Finally it was centrifuged again to obtain supernatant, filtered with 0.22 uM PES filter and further diluted in water.

Quantitative Detection of Spm by UPLC-MS/MS

The quantitation of Spm was performed by Ultra-high Performance Liquid Chromatography coupled with a triple quadrupole mass spectrometer (UPLC-MS/MS). LC separation was done by an Agilent 1290 Infinity Quaternary LC System while mass analyzing was done by an Agilent 6460 Triple Quadrupole mass spectrometer equipped with an Agilent Jet Stream technology electrospray ionization source. The column used was an Agilent EclipsePlus C18 RRHD (2.1×50 mm, 1.8 μm) protected with an Agilent SB-C18 guard column (2.1×5 mm, 1.8 μm).

The LC elution profiles were optimized as follows: Eluent A was water with 0.1% HFBA while eluent B was acetonitrile with 0.1% HFBA. Eluent A was decreased from 95% to 60% in 10 minutes. The gradient was then decreased from 60% to 10% of eluent A in 1 minute. Afterwards the gradient was held constant for 5 minutes. The gradient was then increased from 10% to 95% in 1 minute, followed by being held constant for 8 minutes. (Total run-time=25 minutes).

Autosampler and column temperature were set as 4° C. and 35° C. respectively. Injection was achieved by 5-second needle wash in Flush Port mode for 3 times with eluent B. In each time 10 μL was injected.

For the source parameter, drying gas (nitrogen) temperature was set as 300° C. with 5 L/min flow rate. Nebulizer pressure was 45 psi. Sheath gas temperature was set as 250° C. with 11 L/min flow rate. Capillary voltage was set as 3,500V. For mass detection, scheduled multiple reaction monitoring (MRM) was performed.

Determination of the Binding Affinity and Selectivity of Compounds of Formula 1 with Spm/Spd in Aqueous Solution The developed compounds of Formula 1 (including compounds A-E below) were examined through fluorescence and fluorescence lifetime titrations with various concentrations of the target Spm/Spd in solution and in biological media (simulated level of Spm-1.2 μM/Spd-11.9 μM in urine/blood). The physiological properties and detection limits of these sensors for Spm/Spd were also determined. Measurements were taken after attaining equilibrium, and the emission of the europium was monitored. Luminescent responses in terms of $I_0/(I-I_0)$ (where I and $I_0$ are the measured and blank luminescence intensities, respectively)

were plotted as a function of the analyte concentration. For the determination of the binding strengths of the various analyte adducts, a series of analyte solutions at known concentrations were mixed with the Spm/Spd solutions at various concentrations. The binding constant, $K_B$, was estimated from the ratio between the y-intercept and the slope that is to be obtained from the line of best fit using Benesi-Hildebrand equations. The signal changes of the lanthanide complex after binding with Spm/Spd may be induced by various mechanisms, such as the electron transfer process (Rehm-Weller equation) and redox potentials, and transient absorption with flash photolysis have been applied to understand the mechanism responsible for the change of the signal after the inventor's lanthanide systems tagging Spm/Spd.

Test Compounds:

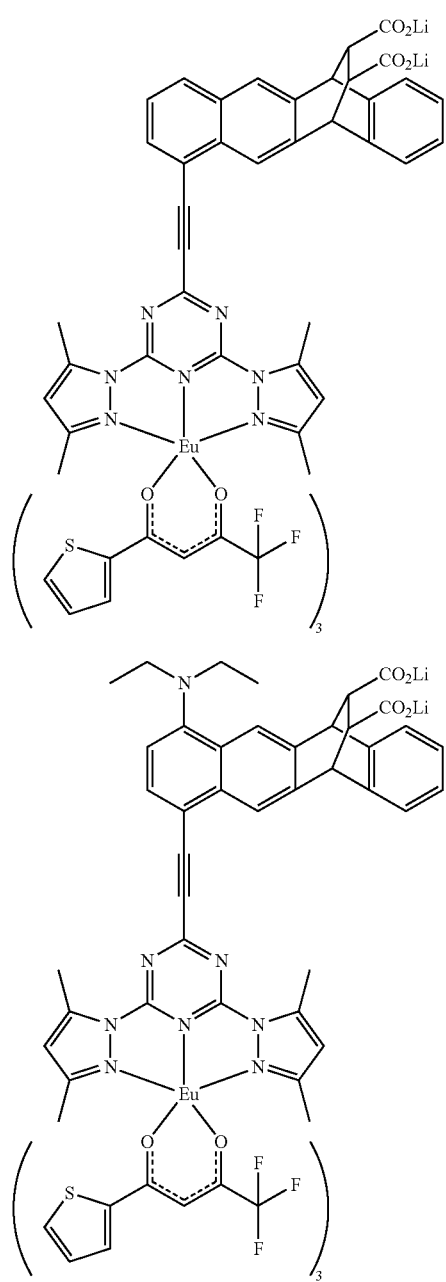

A

-continued

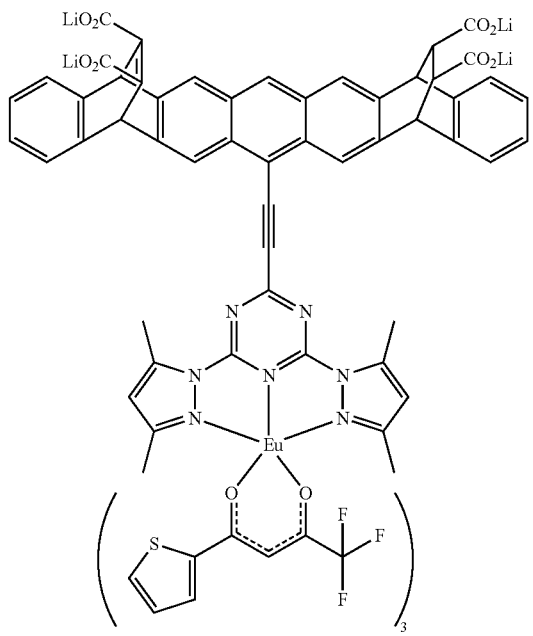

C

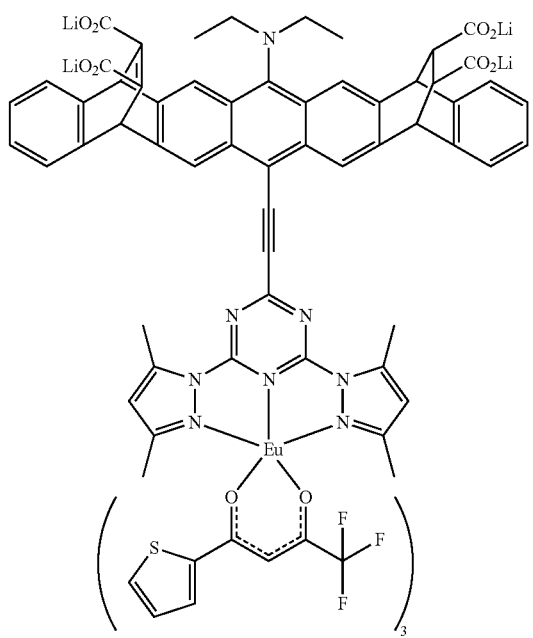

B

D

-continued

E

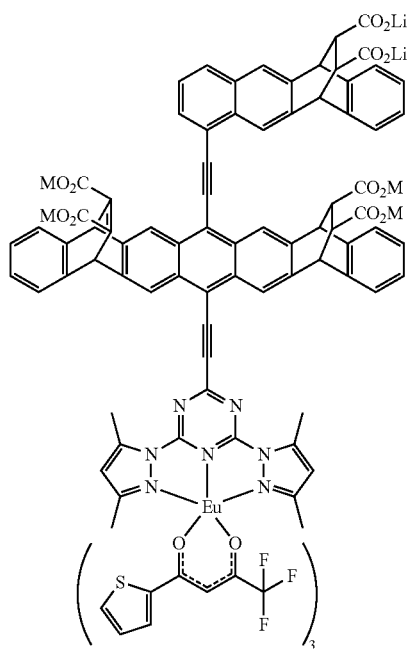

The results of the binding and selectivity experiments are presented in the table below. The selectivity assay was conducted in samples containing 500 ppb of the amines listed in last column.

| Compound | Detection limit (Spermine) | Selectivity (Spermine) | Color Change | Amines present in sample |
|---|---|---|---|---|
| A | 800 ppb | Good | Mild color change Yellow to Pale Pink | Tryptamine n-butyamine n-proppylamine histine glycine ethanolamine cysteine glutamic acid GABA |
| B | 500 ppb | Good | Mild color change Yellow to Pale Pink | Tryamine Tryptamine n-butyamine n-proppylamine histine glycine ethanolamine cysteine glutamic acid GABA |
| C | 1 ppm | Poor | No color change | — |
| D | 500 ppb | Excellent | Significant Yellow to Pale Pink | Spermidine Cadaveine Putrescine Histamine Tryamine Tryptamine n-butyamine n-proppylamine histine glycine ethanolamine cysteine |
| E | 600 ppb | Good to Excellent | Significant Yellow to Pale Pink | glutamic acid GABA Spermidine Cadaveine Putrescine Histamine Tryamine Tryptamine n-butyamine n-proppylamine histine glycine ethanolamine cysteine glutamic acid GABA |

INDUSTRIAL APPLICATION

The present disclosure relates to the detection of urinary polyamines for prostate cancer biomarkers. In particular, the present disclosure provides a novel, highly-sensitive and specific, and color-changing polyamines tracer with the use of lanthanide complexes as prostate cancer diagnostic biomarker for early prostate cancer screening, which has a great potential to be applied in clinical diagnosis.

I claim:

1. A compound of Formula 1:

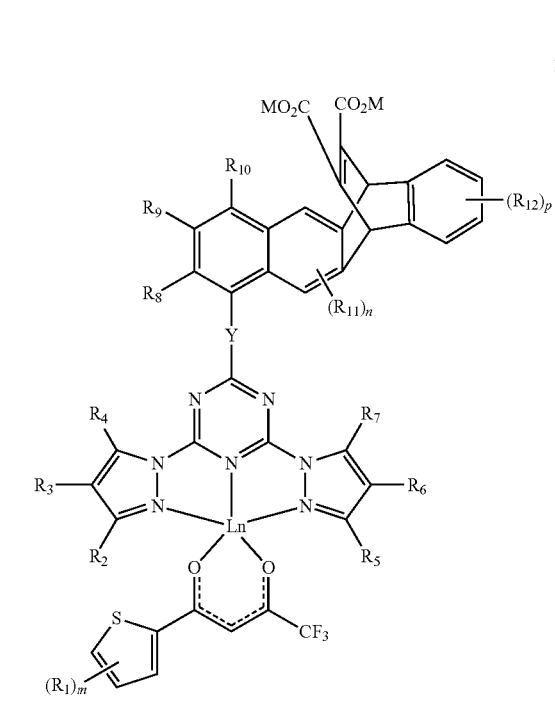

wherein, m is 1, 2, or 3;

n for each occurrence is independently 1 or 2;

p for each occurrence is independently is 1, 2, 3, or 4;

Ln is a lanthanide;

each M is independently selected from the group consisting of Na, Li, and K; or two M taken together represent Mg or Ca;

Y is —C≡C— or is absent;

$R_1$ for each instance is independently hydrogen, alkyl, or cycloalkyl;

each of $R_2$, $R_3$, $R_4$, $R_5$, $R_6$, and $R_7$ are independently selected from hydrogen, alkyl, cycloalkyl and aryl;

each of $R_8$ and $R_9$ are independently selected from hydrogen, halide, cyano, nitro, hydroxyl, ether, thioether, amine, amide, acylamino, ester, alkyl, cycloalkyl, heterocycloalkyl, aryl, heteroaryl, alkene, and alkyne; or $R_8$ and $R_9$ taken together form a moiety selected from the group consisting of:

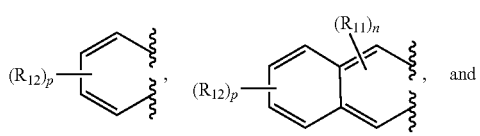

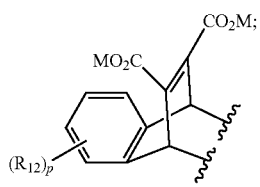

$R_{10}$ is hydrogen, halide, cyano, nitro, hydroxyl, ether, thioether, amine, amide, acylamino, ester, alkyl, cycloalkyl, heterocycloalkyl, aryl, heteroaryl, alkene, or alkyne; or $R_{10}$ is a moiety having the structure:

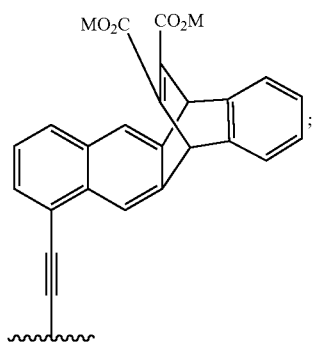

and for each instance of $R_{11}$ and $R_{12}$ is independently selected from hydrogen, halide, cyano, nitro, hydroxyl, ether, thioether, amine, amide, acylamino, ester, alkyl, cycloalkyl, heterocycloalkyl, aryl, heteroaryl, alkene, and alkyne; with the proviso that the compound of Formula 1 does not include a compound of Formula 2:

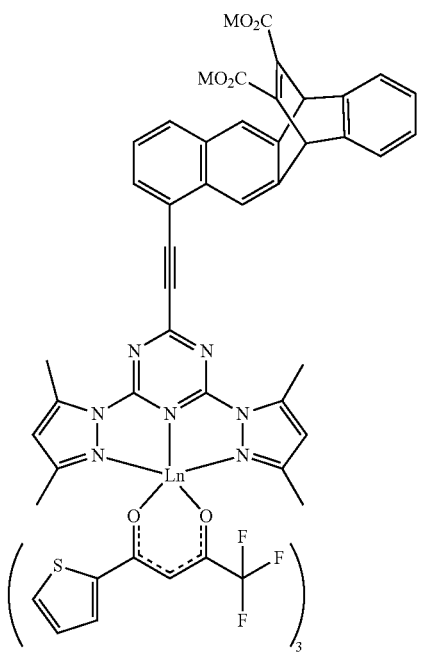

wherein,

Ln is a lanthanide; and each M is independently selected from the group consisting of Na, Li, and K; or two M taken together represent Mg or Ca.

2. The compound of claim 1, wherein each of $R_2$, $R_3$, $R_4$, $R_5$, $R_6$, and $R_7$ are independently selected from hydrogen and alkyl.

3. The compound of claim 1, wherein each instance of $R_{11}$ and $R_{12}$ is independently hydrogen, halide, nitro, cyano, ether, or alkyl.

4. The compound of claim 1, wherein each of $R_8$ and $R_9$ is independently selected from hydrogen, halide, nitro, cyano, ether, and alkyl; or $R_8$ and $R_9$ taken together form a moiety selected from the group consisting of:

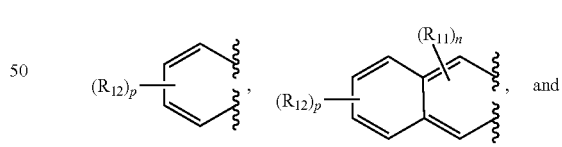

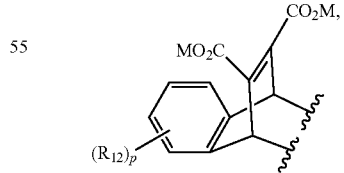

wherein each instance of $R_{11}$ and $R_{12}$ is independently hydrogen, halide, nitro, cyano, ether, or alkyl.

5. The compound of claim 1, wherein $R_{10}$ is hydrogen, halide, nitro, cyano, ether, dialkyl amino, or alkyl; or $R_{10}$ is a moiety having the structure:

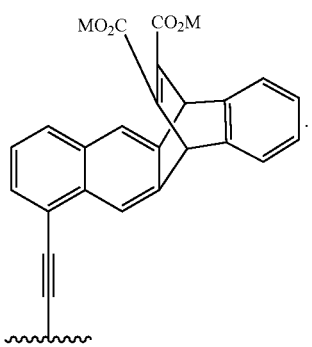

6. The compound of claim 2, wherein each instance of $R_1$, $R_3$, and $R_6$ are hydrogen.

7. The compound of claim 3, wherein each of $R_8$ and $R_9$ is independently selected from hydrogen, halide, nitro, cyano, ether, and alkyl; or $R_8$ and $R_9$ taken together form a moiety selected from the group consisting of:

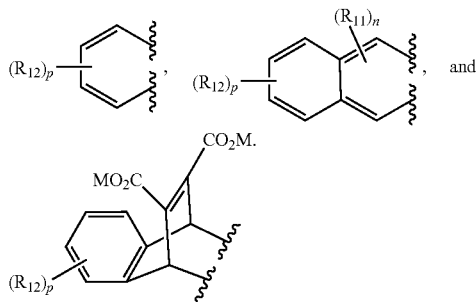

8. The compound of claim 3, wherein $R_{10}$ is hydrogen, halide, nitro, cyano, ether, dialkyl amino, or alkyl; or $R_{10}$ is a moiety having the structure:

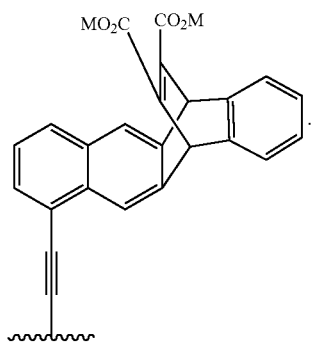

9. The compound of claim 1, wherein m is 1, 2, or 3; n for each occurrence is independently 1 or 2; p for each occurrence is independently is 1, 2, 3, or 4;

Ln is a lanthanide;

each M is independently selected from the group consisting of Na, Li, and K; or two M taken together represent Mg or Ca;

Y is —C≡C—;

$R_1$ for each instance is independently hydrogen or alkyl;

each of $R_2$, $R_3$, $R_4$, $R_5$, $R_6$, and $R_7$ are independently selected from hydrogen and alkyl;

each of $R_8$ and $R_9$ are independently selected from hydrogen and alkyl; or $R_8$ and $R_9$ taken together form a moiety selected from the group consisting of:

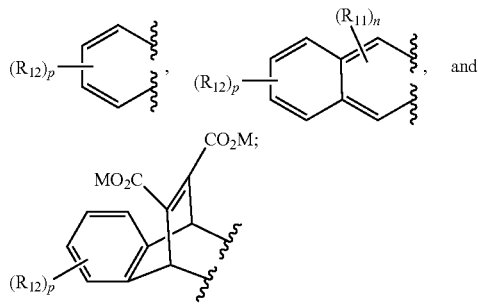

$R_{10}$ is hydrogen, alkyl, and amine; or $R_{10}$ is a moiety having the structure:

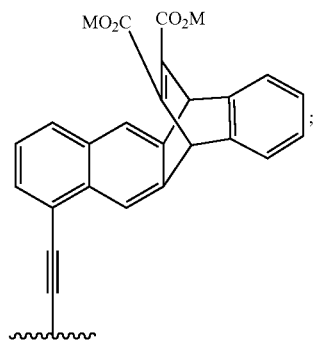

and for each instance of $R_{11}$ and $R_{12}$ is independently selected from hydrogen and alkyl.

10. The compound of claim 1, wherein the compound is selected from the group consisting of:

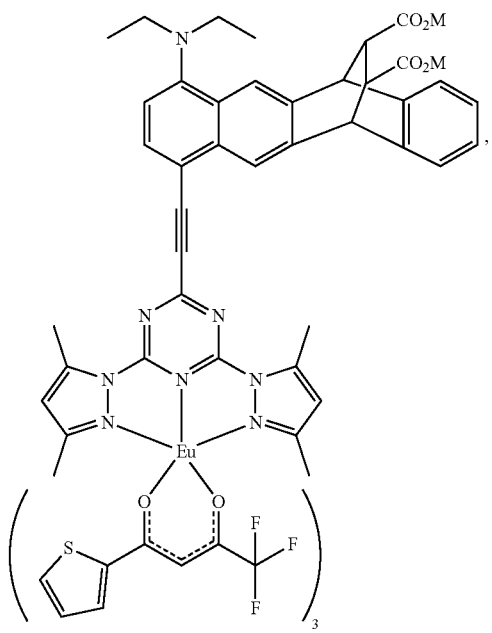

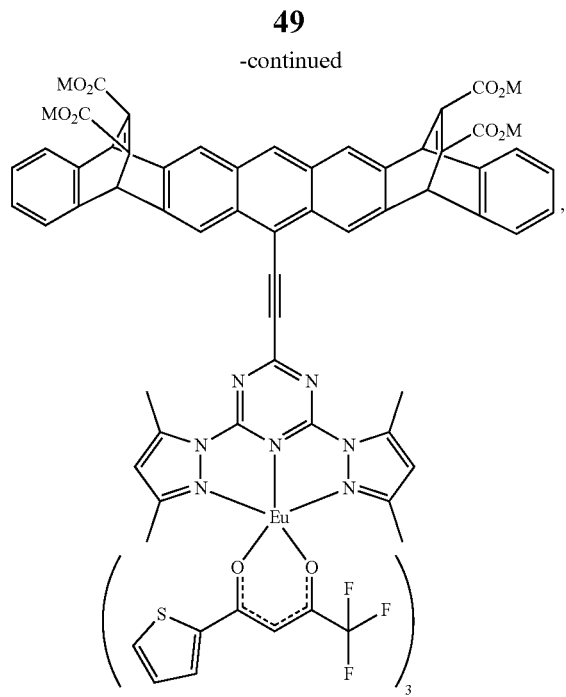

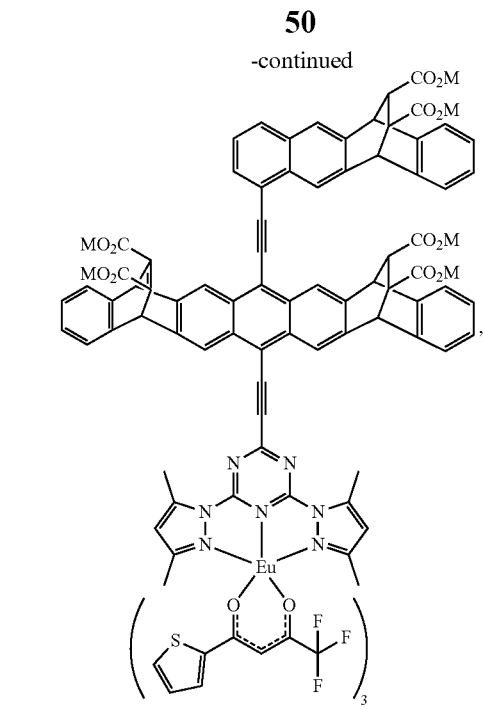

wherein M is lithium or sodium.

11. A method of detecting one or more urinary polyamines, comprising the steps of:
   a. providing a urine sample;
   b. contacting the urine sample with a compound of claim 1 thereby forming a test sample; and
   c. detecting the presence of the one or more urinary polyamines in the test sample.

12. The method of claim 11, wherein the urine sample is obtained from an individual.

13. The method of claim 12, wherein the one or more urinary polyamines is spermine.

14. The method of claim 12, wherein the step of detecting the presence of the one or more urinary polyamines comprises determining the concentration of the one or more urinary polyamines.

15. The method of claim 14, wherein the one or more urinary polyamines is spermine.

16. The method of claim 15 further comprising the step of comparing the concentration of spermine in the test sample with a reference concentration and determining whether the individual has an increased susceptibility to prostate cancer, wherein a decrease in the concentration of spermine in the test sample relative to the reference sample indicates an increased susceptibility to prostate cancer in the individual.

17. The method of claim 16, further comprising the step of conducting a prostate exam on the individual to determine if the individual has prostate cancer and treat the individual with radiotherapy or chemotherapy if the individual has prostate cancer.

18. A method for treating prostate cancer in an individual comprising the steps of:
   d. providing a urine sample from the individual;
   e. contacting the urine sample with a compound of claim 1 thereby forming a test sample;
   f. determining the concentration of spermine in the test sample;
   g. comparing the concentration of spermine in the test sample with a reference concentration and determining whether the individual has an increased susceptibility to prostate cancer, wherein a decrease in the concentration of spermine in the test sample relative to the reference sample indicates an increased susceptibility to prostate cancer in the individual;

h. conducting a prostate exam on the individual to determine if the individual has prostate cancer; and i. treating the individual with radiotherapy or chemotherapy if the individual has prostate cancer.

19. The method of claim 18, wherein the step of determining the concentration of spermine comprises comparing the color of the test sample with a calibrated reference color chart.

20. The method of claim 18, wherein the individual is a human.

\* \* \* \* \*